United States Patent [19]
Oishi et al.

[11] Patent Number: 5,643,642
[45] Date of Patent: Jul. 1, 1997

[54] POLYMERIC METAL OXIDE MATERIALS AND THEIR FORMATION AND USE

[75] Inventors: Tomoji Oishi, Hitachi; Ken Takahashi, Tohkai-mura; Teteuo Nakazawa, Tomobe-machi; Shigeru Tanaka; Tadahiko Miyoshi, both of Hitachi, all of Japan

[73] Assignee: Hitachi, Ltd., Tokyo, Japan

[21] Appl. No.: 475,090

[22] Filed: Jun. 7, 1995

Related U.S. Application Data

[62] Division of Ser. No. 229,092, Apr. 18, 1994, Pat. No. 5,460,877, which is a continuation of Ser. No. 855,672, Mar. 23, 1992, abandoned, which is a division of Ser. No. 569,720, Aug. 20, 1990, Pat. No. 5,234,556.

[30] Foreign Application Priority Data

Aug. 18, 1989 [JP] Japan ..................... 1-211356
Jul. 11, 1990 [JP] Japan ..................... 2-181454

[51] Int. Cl.$^6$ ..................... C09K 19/00
[52] U.S. Cl. ..................... 428/1; 428/336; 428/702; 349/56
[58] Field of Search ..................... 428/1, 336, 702; 359/36

[56] References Cited

U.S. PATENT DOCUMENTS

| 4,623,591 | 11/1986 | Pike | 428/414 |
| 4,680,101 | 7/1987 | Darlington et al. | 204/295 |
| 5,057,335 | 10/1991 | Hanagata et al. | 427/53.1 |
| 5,460,877 | 10/1995 | Oishi et al. | 428/336 |

*Primary Examiner*—Archene Turner
*Attorney, Agent, or Firm*—Antonelli, Terry, Stout & Kraus, LLP

[57] ABSTRACT

A method of treating a metal alkoxide solution to form metal oxide prepolymer molecules therein is characterized by irradiating the solution with light energy having a wavelength selected to break the metal-alkoxy group bond in said metal alkoxide, thereby to form the metal oxide prepolymer molecules in the solution. The prepolymer is converted into polymeric metal oxide gel. The stoichiometry of the oxide is high. A gel of carbon content below 4 atomic % can be achieved by the step of decarbonizing the gel, preferably using light to produce ozone.

2 Claims, 12 Drawing Sheets

POLYMERIC METAL OXIDE MATERIALS AND THEIR FORMATION AND USE

This application is a Divisional application of Ser. No. 229,092, filed Apr. 18, 1994, now U.S. Pat. No. 5,460,877, which application is a continuation application of Ser. No. 855,672, filed on Mar. 23, 1992, (now abandoned), which application is a divisional application of Ser. No. 569,720, filed Aug. 20, 1990 (now U.S. Pat. No. 5,234,556).

BACKGROUND OF THE INVENTION

1. FIELD OF THE INVENTION

This invention relates to polymeric metal oxide materials and their formation from metal alkoxide solutions and to articles including such polymeric metal oxides especially in the form of thin films. The invention also provides a composition for use in forming such a polymeric metal oxide.

2. DESCRIPTION OF THE PRIOR ART

Various methods are known for producing metal oxide films. Many of these methods do not produce a polymeric metal oxide. A polymeric metal oxide film is a ceramic material which is desirable to produce without a firing step, since the high temperature of firing makes it impossible to form the film directly on a substrate which has low heat-resistance. Particular uses of such oxide films are as insulation films and corrosion resistant films.

Known methods of forming an oxide film include the sputtering method, which is a physical film-forming method, such as described on pages 1362 to 1366 of Journal of Vacuum Science Technology A (J. Vac. Technol. A), Vol. 1, No. 3 (1985) and the chemical vapor deposition process (CVD process), which is a chemical film-forming method, such as described on page 927 of Journal of Electrochemical Society (J. Electrochem. Soc.), 120 (1973).

The sputtering method includes a high-frequency sputtering method using an oxide as the target, a method of forming a metal thin film while using a metal as the target and thermally oxidizing the film, and a method of forming an oxide thin film by reactive sputtering (using Ar+$O_2$ as the sputtering gas).

The CVD process includes a thermal CVD process using a metal chloride as the raw material, and an optical CVD process aiming at film formation at a lower temperature such as is disclosed in JP-A-61-190074 (1986).

Further, there is also known, as a chemical film-forming method, the sol-gel method, in which growth occurs in liquid. Although long known for production of for example porous silica, the sol-gel method, such as described on pages 725 to 730 of Material Research Society Symposium Proceedings (Mat. Res. Symp. Proc.) 73, (1986) has recently attracted attention as a low-temperature oxide film-forming method. Reference is also made to JP-A-62-97171 (1987) and JP-A-53-149281 (1978).

There is also known a film-forming method of reacting various silane compounds containing a light activating catalyst such as a-hydroxy ketone so as to produce a reticulate structure having three-dimensional crosslinks, and hardening the reticulate structure by increasing the crosslinks by light radiation (pages 429 to 436 of the XIVth International Congress on Glass (XIV Intl. Congr. on Glass) 1986).

Some disadvantages of these known methods are as follows.

Of the above-described methods, the sputtering method is performed under a high vacuum, and produces a film having many oxygen defects, thereby making it impossible to obtain a film having a stoichiometrical composition or even close to such a composition. In addition, argon gas and the like which are used as the sputtering gas tend to remain in the film, and the oxygen defects and the residual gas exert deleterious influence on the property of the thin film.

The thermal CVD process requires a high temperature, such as not lower than 600° C., in order to obtain a metal oxide film by the hydrolysis of a metal halogenide, which is a raw material.

The optical CVD method is a method of forming a film at a lower temperature by utilizing light energy for the decomposition reaction of a raw material. It is, however, impossible that the light energy provides all the reaction energy for the decomposition of the raw material and the reaction of the decomposed raw material with oxygen, and it is necessary to provide heat and to heat the substrate. Although this method increases the growth rate of an oxide thin film, the film quality is equal to that of the film obtained without radiation of light.

In the method of thermally oxidizing a film after the sputtering or CVD process, a heating step is essential, so that it is difficult to form a film on a substrate having a low heat resistance such as an organic substrate, or a substrate having a large difference in the thermal expansion coefficient compared with the film. Both the sputtering method and the CVD process require a large-scale vacuum apparatus. The apparatus is expensive and the formation of a film on a large area is difficult.

The sol-gel method is a method of synthesizing an inorganic polymer, which is a ceramic material, at a temperature approximate to room temperature by a chemical reaction in a solution. However, since a metal alkoxide, which is an organic compound, is used as a raw material, carbon tends to remain the the product. In addition, the reaction takes an inconveniently long time. Although a step of heat treating after film formation is known, the heating produces a problem if the substrate has low heat resistance. Even if ultraviolet radiation is used on the film, it is not possible to avoid large amounts of residual carbon.

The method of radiating light on various silanes containing light activating catalyst aims at increasing three-dimensional crosslinking, and removal of an organic substance from the film is not taken into consideration.

In the light of the present invention described below, some comments on some of the specific prior art items mentioned above and some others can usefully be made.

In the method of JP-A-61-190074 (1986) ultraviolet light is directed at the alkoxide molecules $M(OR)_n$ (where M is a metal) which are present in the gas phase in a CVD process, to accelerate decomposition of the alkoxide to the metal oxide. The metal oxide molecules deposit on a substrate in an unpolymerized state. Thus the film produced is not polymeric.

JP-A-62-97151 (1987) describes a sol-gel method of forming a recording film of an optical information storage disc. The film is made of $Sb_2O_3$. Light is not used in the film formation.

JP-A-53-149281 (1978) discloses a sol-gel process in which a monomer, tetramer or octamer of $Ti(OR)_4$ is dissolved in hexane and isobutylalcohol. The solution is coated on a thin polyester film and hydrolysis of the alkoxide is performed to create a polymeric oxide gel. The gel is then subjected to irradiation with ultraviolet light (from a Hg lamp) to produce a hydrophilic film. This irradiation step effects decarbonization of the previously formed gel.

In JP-A-64-87780 (1989) there is described a process in which similarly an alkoxide solution is coated on a substrate, dried and then irradiated to reduce the carbon content.

JP-A-1-294535 (published 28 November 1989) is concerned with the production of a superconductor powder. $Bi(OR)_3$, $Sr(OR)_2$ and $Cu(OR)_2$ are dissolved in isopropanol containing water, and refluxed to remove the isopropanol and obtain a solid mixture. The solid mixture is irradiated with ultraviolet and infra-red radiation, to obtain the desired mixed oxide powder.

SUMMARY OF THE INVENTION

It is an object of the present invention to reduce or eliminate the above-described problems in the CVD process and the conventional sol-gel method described above.

In particular, it is an object of the present invention to obtain a polymeric metal oxide thin film having a good stoichiometrical composition, i.e. a composition close to stoichiometrical, in a short time.

It is a further object to provide a method of obtaining such a film without the need for heat treatment at a high temperature.

It is yet a further object to enable formation of a film on a large area.

It is another object of the present invention to obtain a good quality thin oxide film which can be applied in electronic devices, e.g. high-capacity thin film capacitors, electroluminescence elements and display units thereof, semiconductor devices, multi-layer printed circuit boards, and in other devices such as optical discs.

It is still another object of the present invention to provide a metal with an amorphous or polymeric metal oxide film formed thereon as an environment-resistant or corrosion-resistant protective film.

The present invention is principally characterized by the step of irradiating a metal alkoxide solution with light energy having a wavelength selected to break the metal-alkoxy group bond in the metal alkoxide or alkoxides, thereby to form metal oxide prepolymer molecules in the solution. The prepolymer may then be converted into polymeric metal oxide gel, which is generally amorphous. A preferred further step is decarbonizing the gel, e.g. by forming ozone.

The solution containing the prepolymer molecules, which are explained further below, may be called a sol, i.e. it can be thought of as containing low molecular weight polymer molecules suspended in solvent. The sol is converted into the gel. Herein, the term "gel" is used, as is conventional, for both the semi-rigid material including solvent molecules and the solid material produced after removal of the solvent.

The present inventors have found that the process of formation of the prepolymer can be accelerated by the irradiation of the metal alkoxide solution with light energy adapted to break the metal-alkoxy group bond (i.e. the M—OR bond). Generally, molecular oxygen is not present at this stage. Additional benefits are obtained in the gel subsequently produced. Particularly, the increased breakage of the M—OR bonds results in increased production of ROH, which is easily removed in the gel formation or subsequently by decarbonization, leading to a lower carbon content in the resulting polymeric oxide. The whole process, including decarbonization using light energy, can be performed at low temperature, avoiding the need for heat treatment. Further, the decarbonization can be conducted at a relatively low oxygen concentration, if desired, resulting in reduced ozone production and less damage to the substrate.

In the context of the present invention, the metal element of the metal alkoxide may be any element capable of forming a solid polymeric oxide, including therefore some elements, such as P, Si and Se which in other contexts exhibit non-metallic characteristics.

In one aspect, the invention provides a method of forming a polymeric metal oxide gel, comprising the steps of
(i) forming a metal oxide prepolymer in solution, by irradiating a metal alkoxide solution with light energy having a wavelength selected to break the metal-alkoxy group bond in said metal alkoxide, and
(ii) converting said prepolymer to polymeric metal oxide gel.

The step (ii) of conversion of the prepolymer to gel may under suitable conditions take place with the passing of time, but preferably comprises as least one of
(a) after or simultaneously with step (i), irradiating with light energy so as to form the gel,
(b) heating the prepolymer solution to form the gel,
(c) removing solvent from the prepolymer solution sufficiently to cause formation of the gel.

The decarbonizing step preferably comprises irradiating the gel with light energy, in the presence of a substance producing oxygen radicals, e.g. molecular oxygen. Such irradiation preferably causes production of ozone.

The whole process is preferably performed below 300° C.

Typically the gel is formed as a thin film, preferably having a thickness in the range of 1–1000 nm. The thin film may be formed by contacting a substrate with the prepolymer solution, removing it from the solution and then irradiating it to decarbonize the gel. These steps may be repeated, so as to produce said thin film as a plurality of layers. If the solution contains alkoxides of two or more metals, alternating layers of different metal oxides can be produced, as illustrated below.

Preferably the concentration of metal alkoxide in the solution in the step of prepolymer formation is in the range 0.0025–2.5 mol/l. The alkoxide solution typically has one or more alcohols as solvent and, to promote the polymerization reaction may contain water or an organic acid.

In another aspect, the invention provides a method of forming a polymeric metal oxide gel comprising the step of irradiating a metal alkoxide solution with light energy having a wavelength adapted to break the metal-alkoxy group bond in said metal alkoxide, so as to achieve formation of polymeric metal oxide. Subsequent to the irradiating step, there is preferably a step of decarbonizing the polymeric metal oxide, as already described.

The invention further can provide a method of reducing the carbon content in a polymeric metal oxide gel.

Especially because of the increased effectiveness of decarbonization, due to the breaking of the M—OR bond by light, the invention can provide novel products. Thus the invention further provides an amorphous polymeric metal oxide containing C—H bonds and having a total carbon content in the range of 0.01 to 4 atomic %. The C—H bonds are derived from organic radicals present in the formation of the oxide. The content of oxygen may be at least 85% of stoichiometric. The molecular weight of the polymer is typically greater than 20000.

In another aspect, the invention provides an article comprising a substrate and on the substrate a film of amorphous polymeric metal oxide containing C—H bonds and having a total carbon content of 0.01 to 4 atomic %, said substrate having a melting point of not higher than 300° C.

In yet another aspect, the invention provides a composition for use in forming a polymeric metal oxide gel, comprising a solution containing (i) at least one alcohol, (ii) water or an organic acid and (iii) a metal oxide prepolymer, wherein the carbon content in said prepolymer is not more than 8 atomic %.

Examples of application of the polymeric metal oxide film of the present invention will be described in the following:

(a) An electroluminescence element provided with a substrate, a light-emitting layer and between them the polymeric metal oxide insulating film. Such a film can have a withstand voltage of not less than 2.8 MV/cm.

(b) A thin film capacitor having as a dielectric the polymeric metal oxide film.

(c) A metal member having the polymeric metal oxide film on the surface thereof, as a corrosion-resistant film.

(d) An integrated circuit device having a protective film on the surface thereof, in which the protective film is composed of the polymeric metal oxide film.

(e) A display unit comprising a substrate and transparent electrodes, a first insulating layer, a patterned light-emitting layer, a second insulating layer and upper electrodes formed on the substrate in that order, wherein the transparent electrodes, the first insulating layer and the second insulating layer are each composed the polymeric metal oxide thin film. Such a display device can be driven by a voltage of not more than 200 V.

(f) An optical disc comprising a transparent substrate and a recording medium composed of the high-molecular metal oxide provided on the substrate.

Without wishing to limit the invention, some more explanation of the chemical principle will now be given.

A metal alkoxide used in the present invention is a substance represented by the general formula $M(OR)_n$ (M is metal, R is alkyl group, n is an integer). A metal alkoxide absorbs reaction energy in the presence of water, and produces by hydrolysis reaction a compound represented (RO)$_{n-1}$MOH which has a structure in which one of the alkoxy groups is substituted by a hydroxyl group. Such an intermediate product produced by partial hydrolysis reacts with another metal alkoxide molecule, and grows as the condensation product:

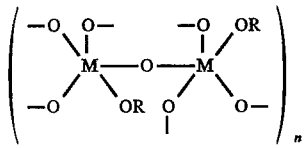

This prepolymer contains the metalloxane linkage M—O—M. By the sol-gel method, there is thus synthesized an inorganic polymer, namely, an oxide on the basis of the above-described chemical reactions, namely, hydrolysis reaction and condensation reaction. In the sol-gel reaction, the rate-determining step of the reaction is thought to be the cleavage of the metal-alkoxy group bond in the hydrolysis reaction.

The presence of water may be disadvantageous in some products, e.g. electronic devices. In place of the hydrolysis reaction, within the present invention, a deester condensation reaction may be used to achieve the sol-gel reaction. A nonwater solvent can then be employed. The deesterization reaction makes use of a cocondensation reaction using an organic acid:

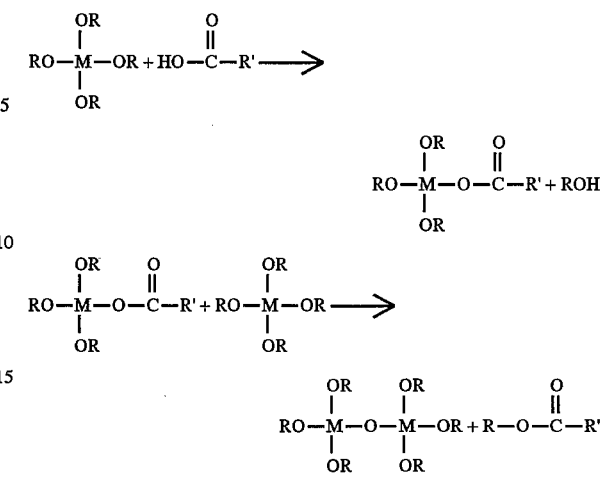

(M; metal, R,R'; $C_nH_{2n+1}$)

In the above reaction, the reaction proceeds in all the directions in three-dimensional manner so that an inorganic polymer is produced.

In the present invention, by radiating light energy having a wavelength which is appropriate for breaking the metal-alkoxy group bond onto a solution containing a metal alkoxide as an effective ingredient, the metal-alkoxy group bond is selectively broken, thereby accelerating the hydrolysis or deester reaction, for the purpose of polymerization, and the sol-gel reaction is completed with the metal oxide having a highly stoichiometrical composition. In order to reduce the amount of organic material in the oxide by oxidizing the small amount of organic substance remaining in the oxide so that preferably the oxygen content of metal oxide is not less than 85% of the stoichiometrical composition or the carbon content remaining in the thin film is 0.01 to 4 atomic %, light having a wavelength which is suitable for producing oxygen radicals, e.g. ozone is radiated onto the oxide. Especially, it is preferable from the point of view of properties that the oxygen content is not more than 95% of the stoichiometrical composition and the carbon content remaining in the thin film is not less than 0.2 atomic %, and under this condition, a thin film of oxide may be obtained in a short time.

Since this process may be performed at a low temperature, the heat treatment for improving the film quality, which has been carried out in the prior art, is not necessary, and the formation of an oxide film on a substrate of resin, paper or the like which has a heat resistance of not higher than 300° C. or on a substrate having a large difference in the thermal expansion coefficient from the oxide film is possible. Excellent electrical characteristics of the oxide film can be obtained.

It is preferred that light radiated onto the alkoxide solution has only the specific wavelength which is appropriate for breaking the metal-alkoxy group bond and for forming the metalloxane bond (M—O—M), thus achieving polycondensation of the metal alkoxide. The desired polymer oxide is obtained with a higher purity by radiating only light having the specified wavelength. Radiation of light having another wavelength involves a possibility of producing a compound other than the desired polymer, which may make it impossible to obtain a polymer having a high purity.

In the present invention, since a film may be formed on a substrate from a solution irradiated with light, it is possible to radiate light onto the film without a special drying step, thereby enhancing the effect of removal of film impurities.

In order to radiate light having a specified wavelength, a monochromator is provided on the light radiating portion so as to enable only light having a specified light to be radiated.

If a laser having a strong directivity is used for light radiation, it is possible to form a fine pattern of an oxide thin film on a substrate.

In the method of the invention, the solution for the sol-gel reaction which is irradiated with light may contain a catalyst such as an acid and an alkali. It is possible to keep the reaction solution stable by maintaining the reaction solution at a low temperature, and to obtain the sol solution suitable for film formation by radiating light during the film formation step.

With the present invention, since light having a specified wavelength is radiated onto a solution containing a metal alkoxide, it is possible to measure the polymerization degree of the metal alkoxide in the solution, and it is possible to form a film on a substrate after the polymerization degree is enhanced as much as possible to obtain a metal oxide thin film having a high purity. It is an advantage of the present invention that, since it is possible to monitor the polymerization degree of the metal oxide by examining the absorption spectrum of the metal oxide or by a light scattering method, a product having stable quality is obtained.

The present invention is effective for example for the metal alkoxides in the following non-exclusive list. The wavelength is appropriately selected in accordance with the metal alkoxide. This wavelength may be found from a peak in the ultraviolet absorption spectrum of the alkoxide. The wavelength chosen need not be at the maximum of the peak, but should be within the peak. Where a mixture of alkoxides is used, the wavelength may be one in the overlap region of the two respective peaks.

$Zn(OC_2H_5)_2$,
$B(OCH_3)_3$,
$Al(i-OC_3H_7)_3$,
$Ga(OC_2H_5)_3$,
$Y(OC_4H_9)_3$,
$Si(OC_2H_5)_3$,
$Ge(OC_2H_5)_4$,
$Pb(OC_4H_9)_4$,
$P(OCH_3)_3$,
$Sb(OC_2H_5)_3$,
$VO(OC_2H_5)_3$,
$Ta(OC_3H_7)_5$,
$W(OC_2H_5)_6$,
$Nd(OC_2H_5)_3$,
$Ti(iso-OC_3H_7)_4$,
$Zr(OC_2H_5)_4$,
$La[Al(iso-OC_3H_7)_4]_3$,
$Mg[Al(iso-OC_3H_7)_4]_2$,
$Mg[Al(sec-OC_4H_9)_4]_2$,
$Ni[Al(iso-OC_3H_7)_4]_3$,
$(C_3H_7O)_2Zr[Al(OC_3H_7)_4]_2$,
$Ba[Zr_2(OC_2H_5)_9]_2$.

Additionally, alkali and alkaline earth metal alkoxides such as $LiOCH_3$, $NaOCH_3$, $Ca(OCH_3)_2$ and $Ba(OC_2H_5)_2$ may be present in the solution of polymer forming metal oxide. The corresponding alkali or alkaline earth metal cation appears in the polymeric metal oxide.

The starting metal alkoxide may be partly polymerized, e.g. a dimer.

As indicated above, the alkoxide may be anionic, e.g. $La[Al(OR)_4]_3$.

Some specific preferred wavelengths for the radiation to break the metal-alkoxy group bond are:

| Metal | Wavelength (nm) |
|---|---|
| Ta | 254 |
| Si | 210 |
| Sb | 250 |
| Ti | 260 |
| In | 270 |
| Sn | 230 |

BRIEF INTRODUCTION OF THE DRAWINGS

Embodiments of the invention will now be described by way of non-limitative example with reference to the accompanying drawings, in which.

Figure 10A:
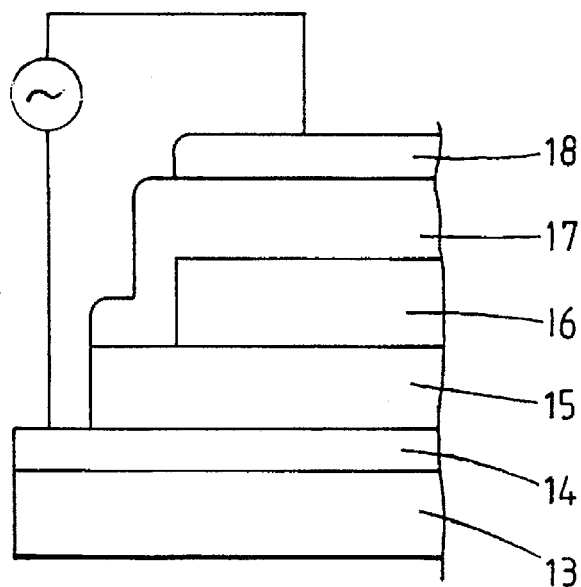
Figure 10B:
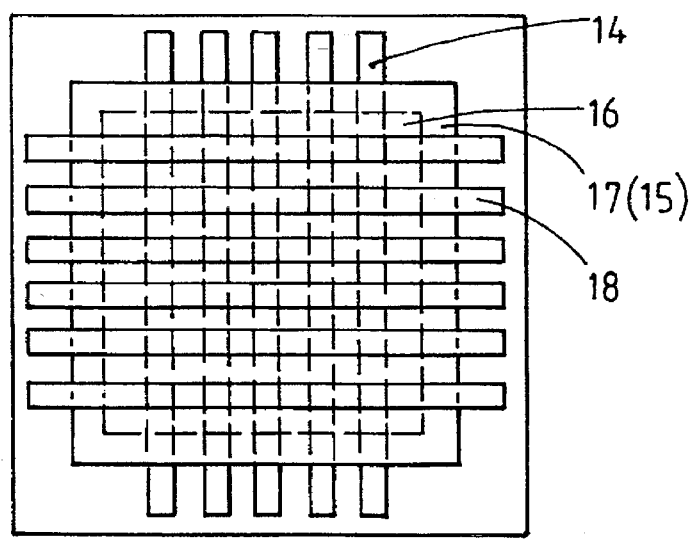
Figure 11:
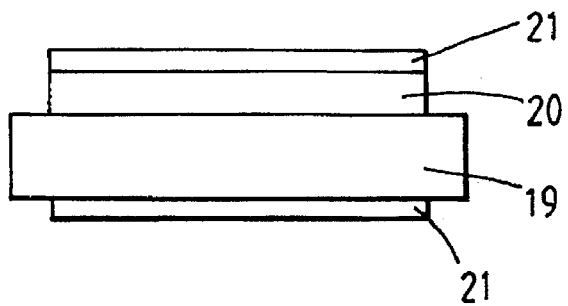
Figure 12:
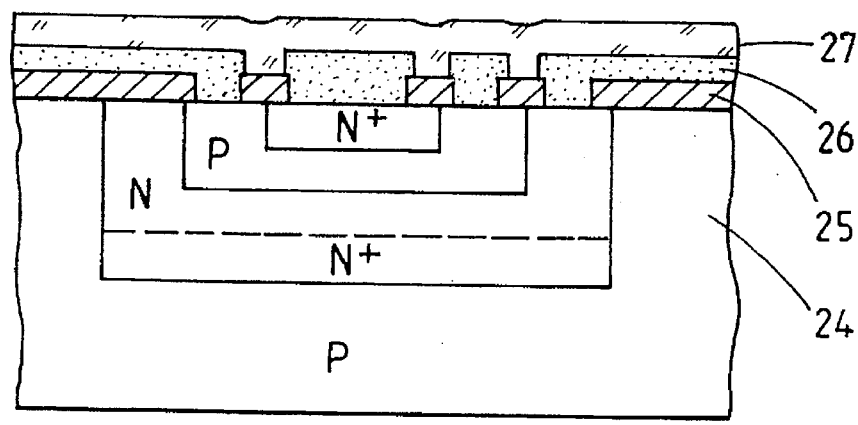
Figure 13:
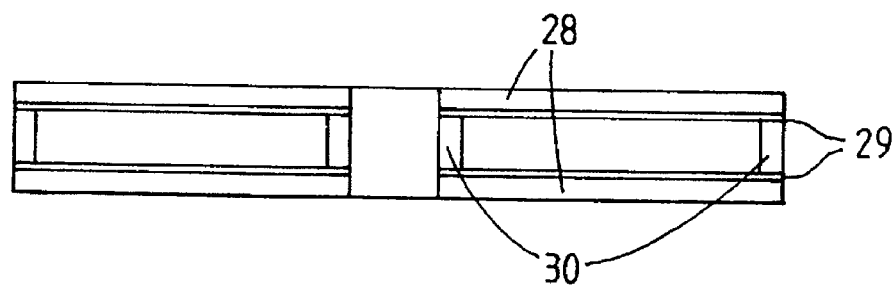
Figure 14:
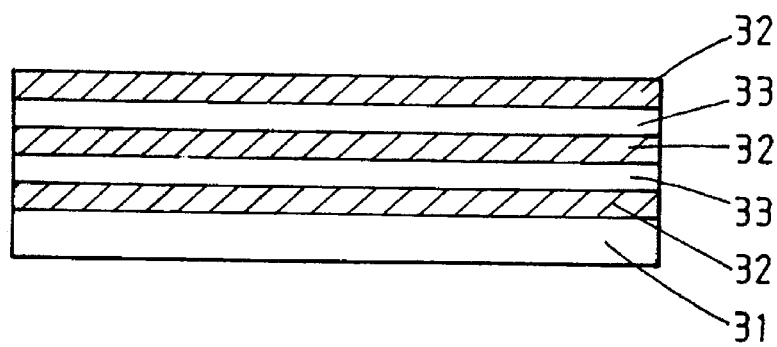
Figure 15:
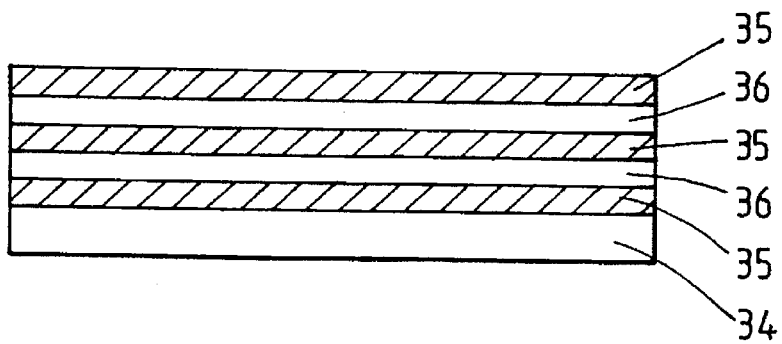
Figure 16:
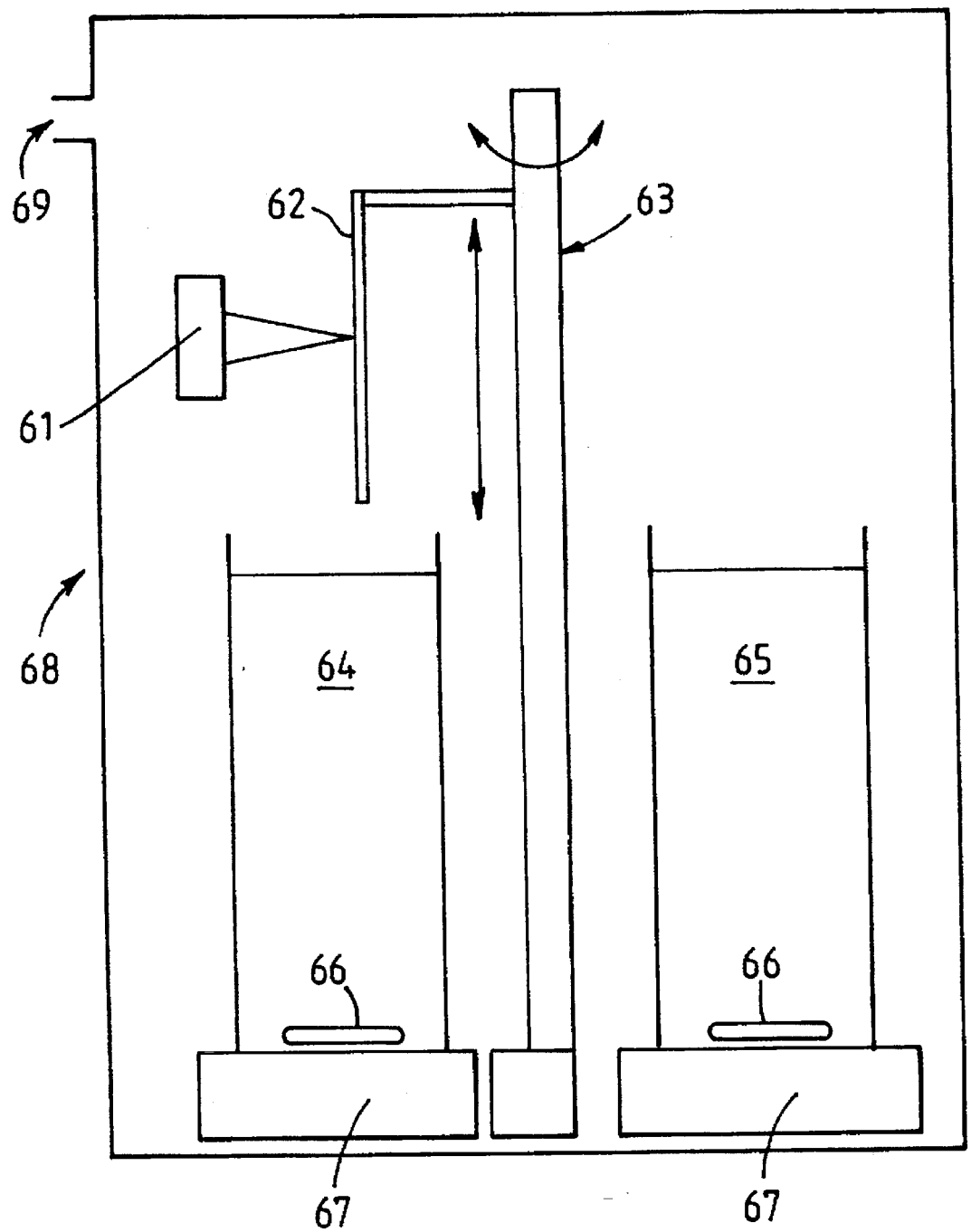
Figure 17A:
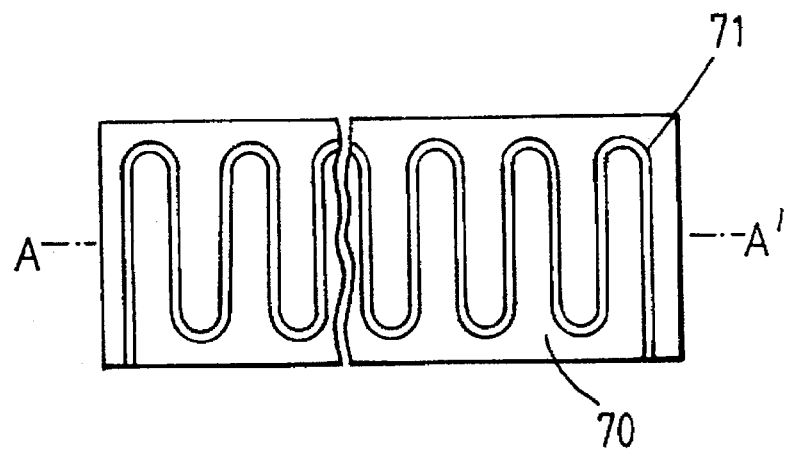
Figure 17B:
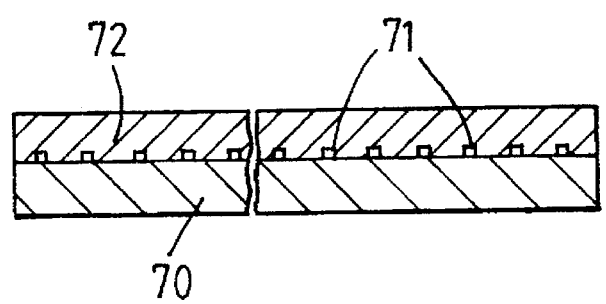
Figure 18:
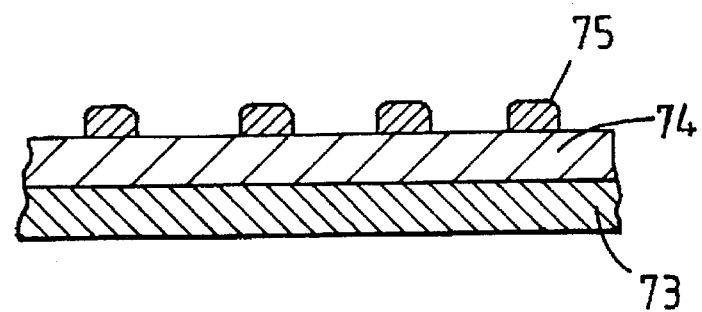
Figure 19:
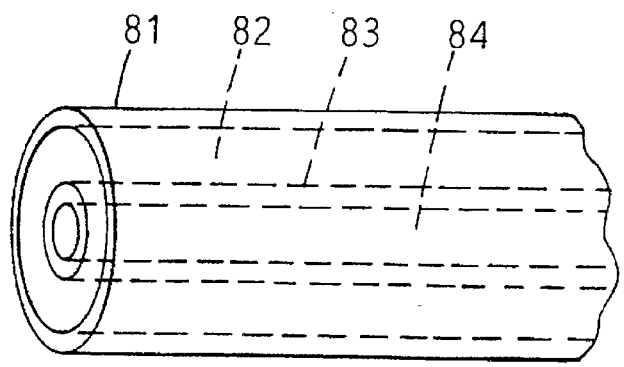
Figure 20:
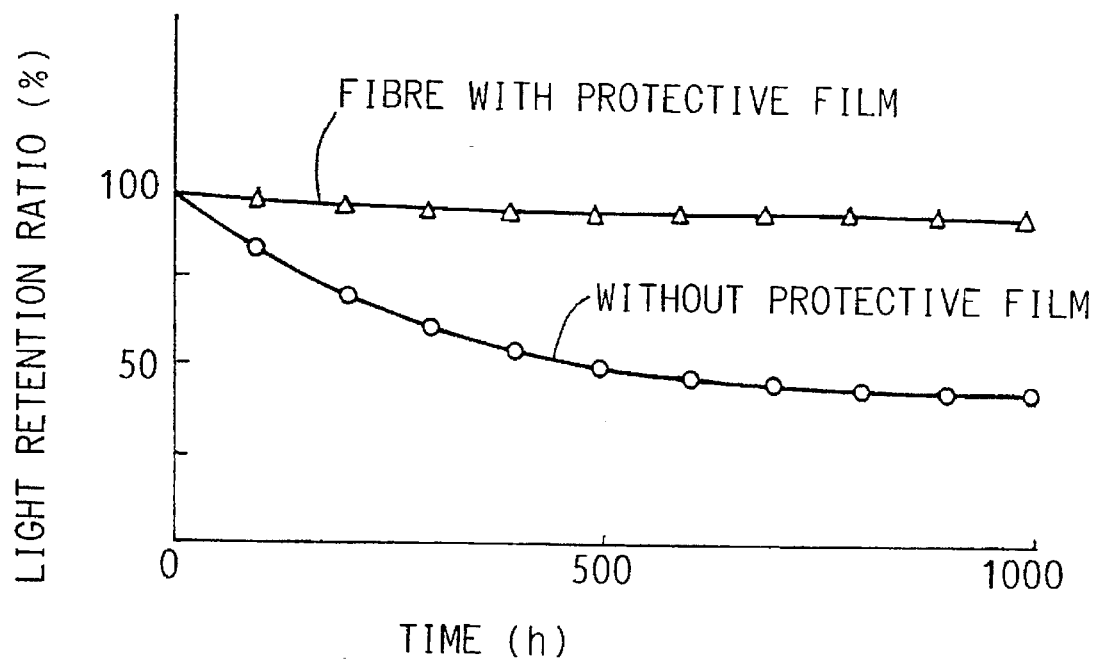
Figure 21:
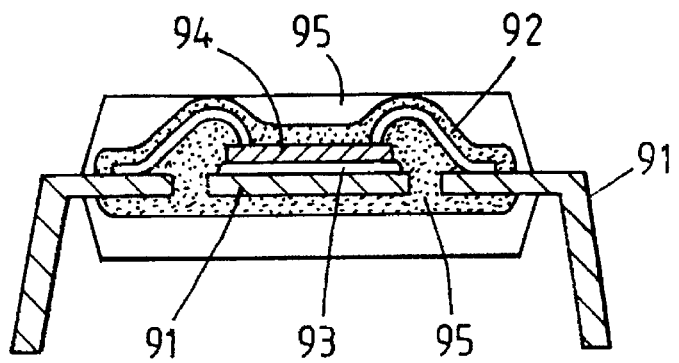
Figure 22:
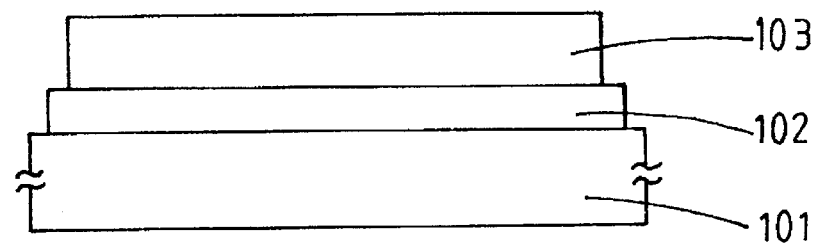
Figure 23:
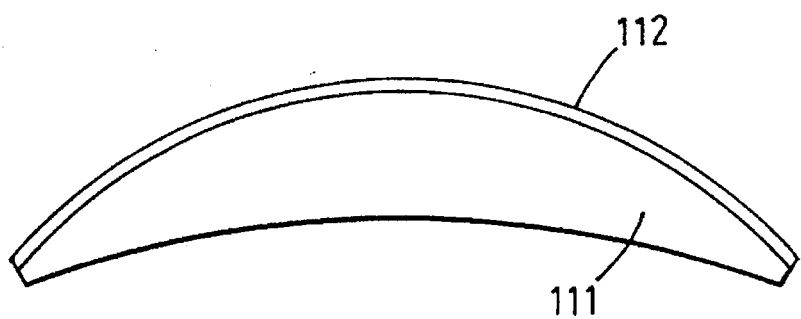
Figure 24:
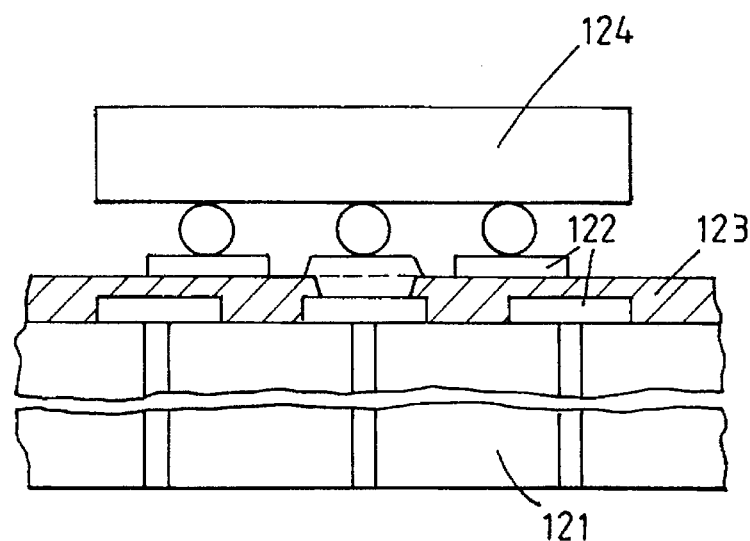
Figure 25:
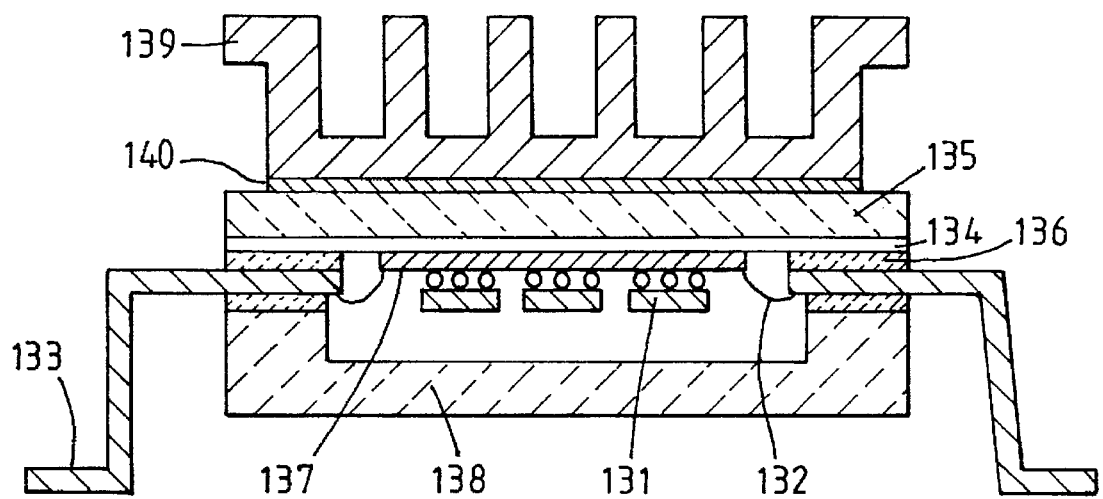

FIGS. 10(A) and 10(B) are respectively a sectional view and a plan view of an electroluminescence element embodying the invention;

FIG. 11 is a sectional view of a thin film capacitor embodying the invention;

FIG. 12 is a sectional view of an integrated circuit device embodying the invention;

FIG. 13 is a sectional view of an optical disk for information storage, embodying the invention;

FIG. 14 is a cross-sectional view of an embodiment in the form of multi-layer $SiO_2$—$TiO_2$ reflection preventing film formed on a polyethylene substrate;

FIG. 15 is a cross-sectional view of an embodiment of the invention in the form of a multi-layer $In_2O$—$SnO_2$ heat flux reflecting film formed on a polyethylene substrate;

FIG. 16 is a diagram of another apparatus for forming films, used for the present invention;

FIGS. 17A and 17B are respectively plan view and sectional view of a device for protection against dew condensation produced by the method of the present invention;

FIG. 18 is a schematic cross sectional view of a portion of a touchpanel component embodying the present invention;

FIG. 19 is a cross-section of a plastics optical fiber having a protective film embodying the invention;

FIG. 20 is a diagram showing test results of oil resistance of plastics optical fibers;

FIG. 21 is a process diagram of resin sealing of a semiconductor element embodying the present invention;

FIG. 22 is a sectional diagram of a $Ta_2O_5$ thin film condenser for a high frequency use embodying the invention;

FIG. 23 is a cross sectional view of a plastics lens with a protective film embodying the invention;

FIG. 24 is a cross sectional view of a silicon chip mounted on a printed substrate with a layer embodying the invention; and FIG. 25 is a cross sectional view of a semiconductor element embodying the invention.

DESCRIPTION OF THE PREFERRED EMBODIMENTS

EXAMPLE 1

Figure 1:
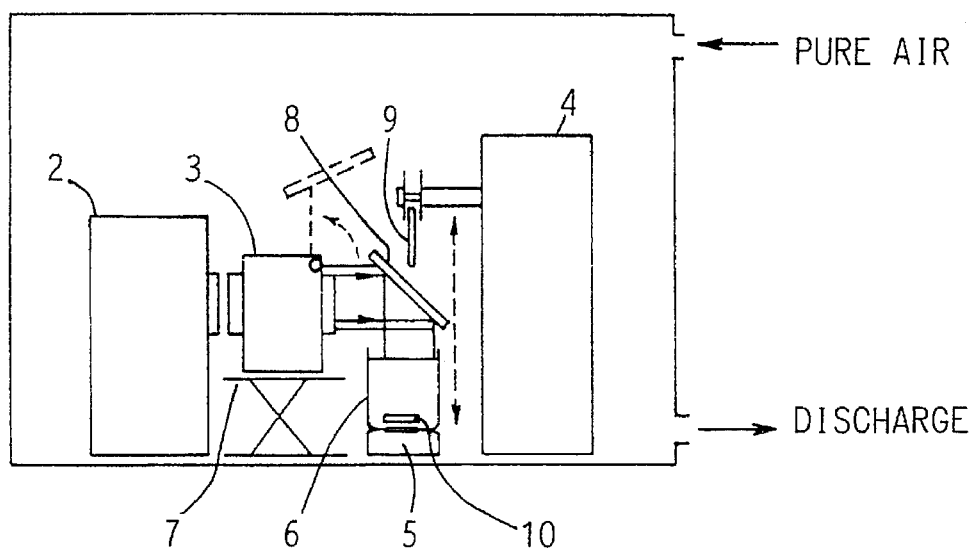
FIG. 1 is a schematic side view of film-forming apparatus used in embodiments of the invention.

FIG. 1 shows the construction of an embodiment of film-forming apparatus for carrying out the present invention.

In a box 1, in which the atmosphere such as air can be exchanged, are provided a light radiating device 2 such as an ultraviolet lamp, a monochromator 3 in which light having a specified wavelength is selectively extracted, a monochromator support 7 for locating the monochromator, and a dipping device 4 for holding and dipping a substrate 9 into a reaction solution accommodated in a beaker 6. The light generated by the light irradiating device 2 is selected on basis of the wavelength by the monochromator and reflected by a mirror 8 so as to be radiated onto the reaction solution accommodated in the beaker 6. In the reaction solution there is a stirrer 10, which is rotated by a magnetic stirring drive 5.

After adequate acceleration of the sol-gel reaction in the solution by irradiation of the light for a predetermined time, the mirror 8 is raised above the monochromator 3 (as shown by broken lines). The substrate 9 is then dipped into the reaction solution for film formation. The substrate 9 is then stopped at a position at which it is irradiated directly with the light which has passed through the monochromator for a predetermined time. At this time, ozone is produced in air and the thin film is oxidized by ozone.

Figure 2:
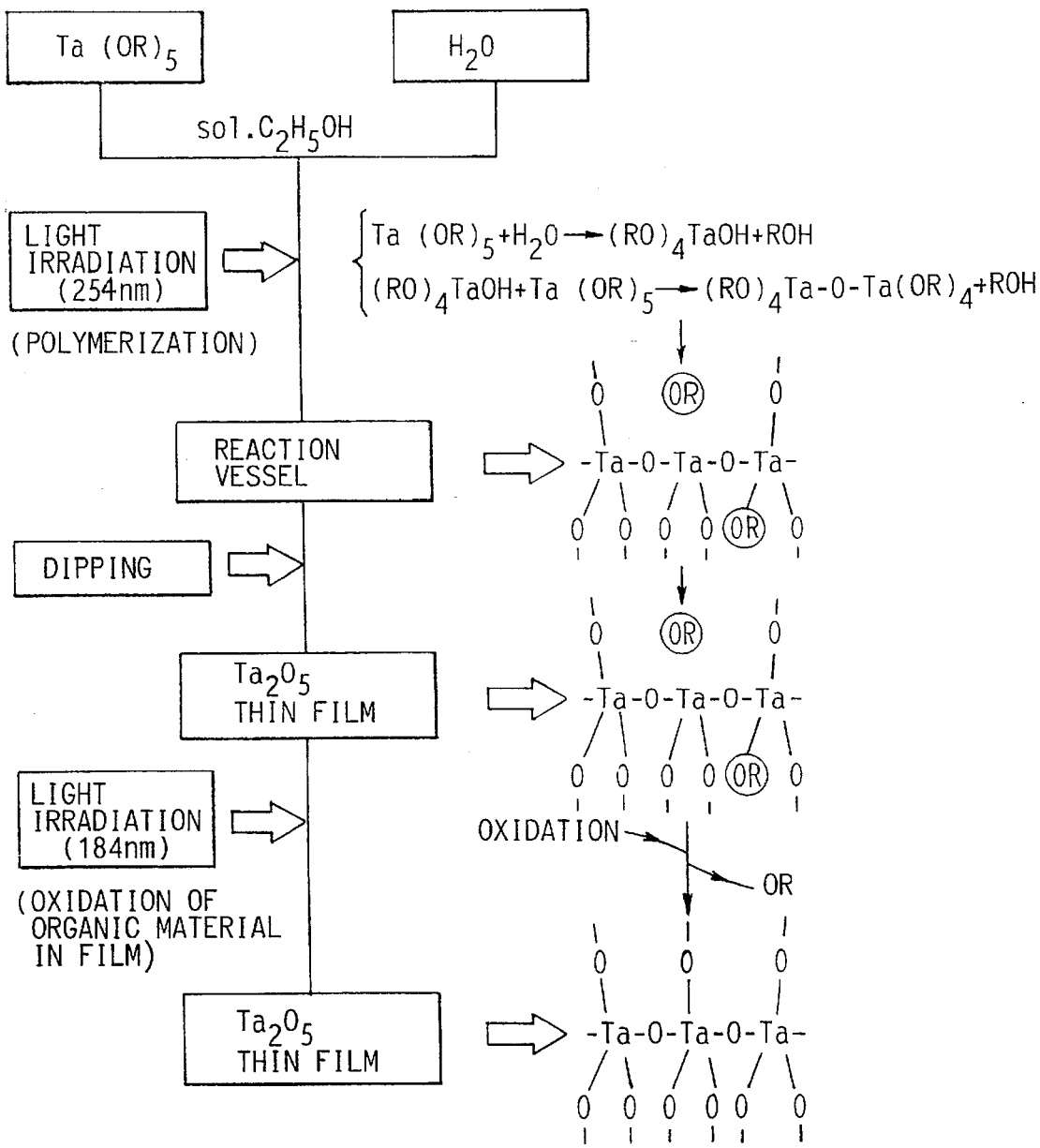
FIG. 2 shows a flowchart of one method of producing a polymeric metal oxide according to the present invention.

A $Ta_2O_5$ thin film was formed by this apparatus in accordance with the flow diagram shown in FIG. 2.

Ethanol solution of 0.5 mol/l of tantalum ethoxide $Ta(OR)_5$ was prepared. To 2 ml of this solution, a solution obtained by adding 2 ml of ethanol to a mixed solution of 8 ml of ethanol solution of 0.5 mol/l of water ($H_2O$) and 2.5 ml of ethanol solution of 0.1 mol/l of hydrochloric acid was added dropwise at a rate of 3 ml/min to obtain a transparent uniform mixed solution. The mixed solution was irradiated with light from a mercury lamp having a wavelength of 254 nm, which corresponds to the tantalum-ethoxy group absorption energy, for 30 minutes and 1 hour respectively for two samples by using the film-forming apparatus shown in FIG. 1. The light intensity was 10 mW/cm².

It is supposed that the light radiation brings about the following reactions which cause the polymerization of Ta oxide and form a prepolymer having a high polymerization degree in the solution:

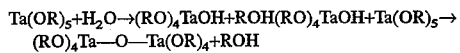

Prepolymer:

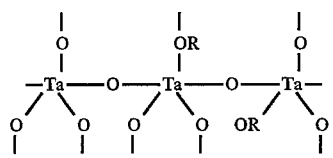

Thereafter, a film was formed of the reaction solution having the prepolymer of a high polymerization degree on the $SiO_2$ substrate by using the dipping device 4 of the film-forming apparatus, and this film was irradiated with light having a wavelength of 184 nm (ultraviolet rays) for about 10 minutes at 3 mW/cm² in order to generate ozone in air. The temperature of the film became about 50° to 60° C. during the light radiation. In this way, an amorphous polymer of tantalum pentoxide having the following molecular structure was formed on the substrate:

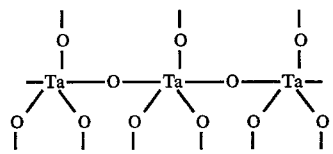

Figure 3:
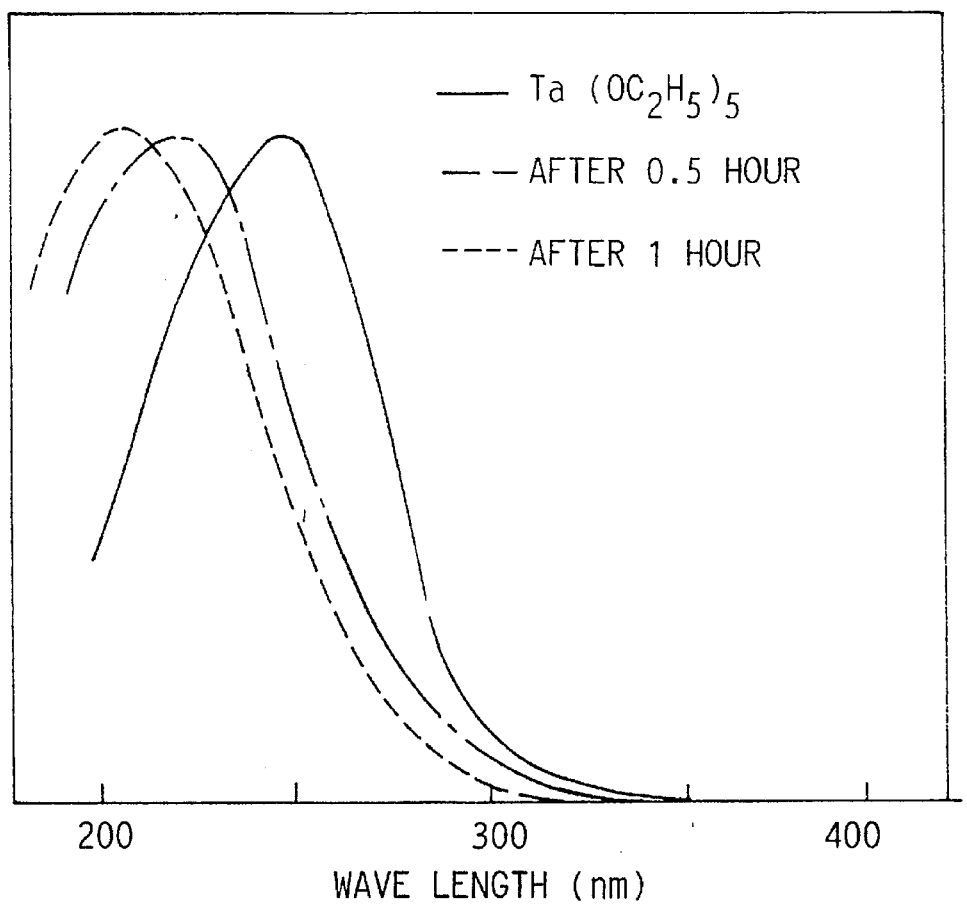
FIG. 3 is a graph showing wavelength against absorption for an alkoxide solution treated according to the invention.

FIG. 3 shows absorption spectra of the reaction solution obtained by irradiating light having a wavelength of 254 nm from a mercury lamp onto an ethanol solution of tantalum ethoxide.. As shown in FIG. 3, the spectral peak moves to the short wavelength side on the radiation of light for 0.5 hour, as indicated by the dot-chain line and moves further on radiation of light for 1 hour which is indicated by the broken line, as compared with the absorption spectral line before the light radiation, which is indicated by the solid line. It is therefore possible to monitor the polymerization of the high-molecular weight tantalum pentoxide prepolymer formed in the reaction solution by monitoring the absorption spectrum.

Figure 4:
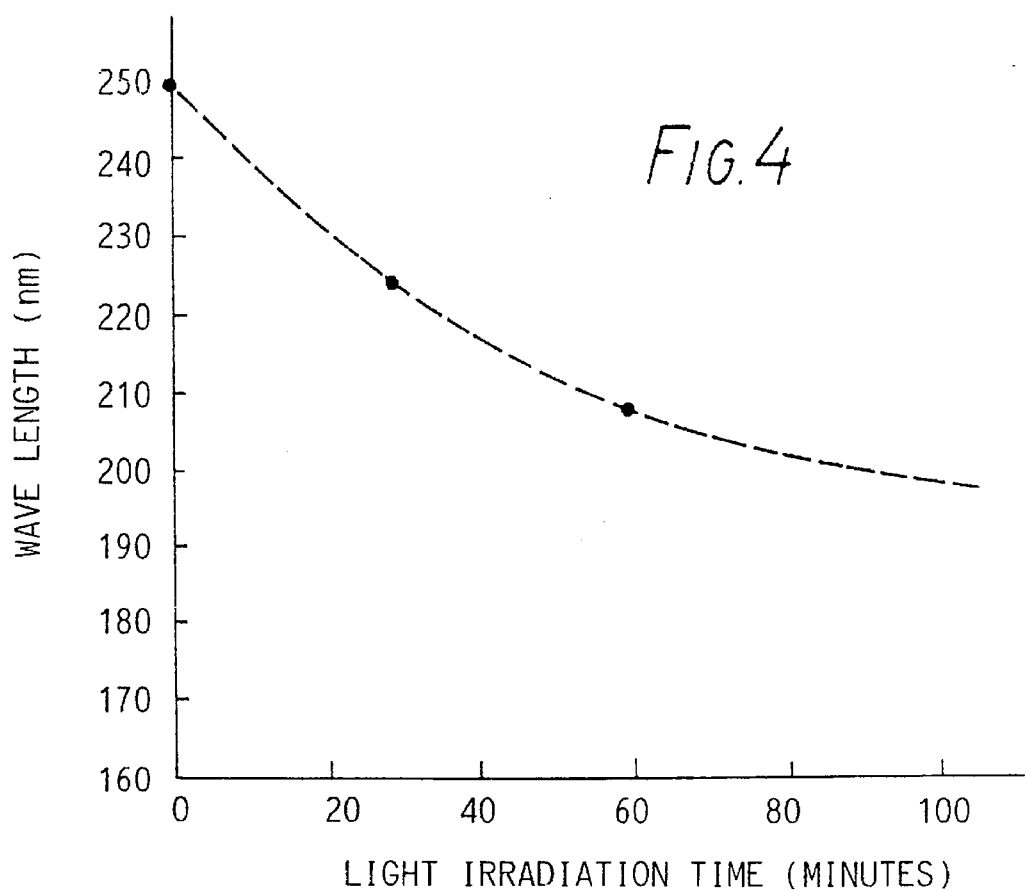
FIG. 4 is a graph showing the relationship between the wavelength and the light irradiation time in FIG. 3.

FIG. 4 is a graph showing the relationship between the time of radiation of light onto the reaction solution and the wavelength at the peak value of the absorption shown in FIG. 3.

The peak values of the absorption wavelengths are 250 nm before light radiation, 224 nm after 30 minutes radiation and 208 nm after 60 minutes radiation. From the peak values, it is assumed that prepolymerization is substantially finished at about 100 minutes radiation. 30 minutes radiation produces about 50% prepolymerization, and 60 minutes radiation about 80% prepolymerization. It is preferred that the prepolymerization degree caused by the light radiation onto the reaction solution should be as high as possible. Especially, not less than 50% of prepolymerization is preferable, and not less than 80% of prepolymerization is more preferable.

The $Ta_2O_5$ polymeric film formed by the above-described method, using 60 minutes irradiation of the ethoxide solution as described above, was compared with a film formed by another method with respect to the infrared absorption spectrum, the amount of organic substance remaining in the film and the stoichiometrical ratio being measured by using ESCA.

Figure 5:
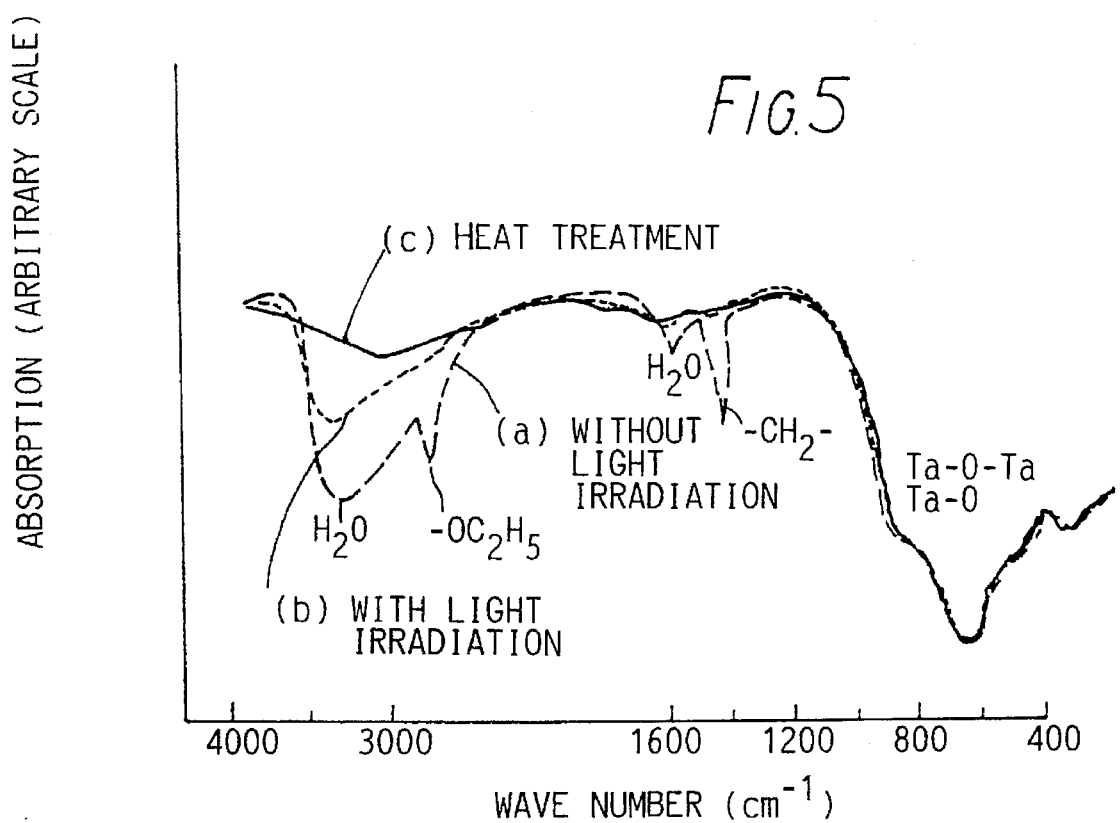
FIG. 5 is a graph showing the relationship between wave number and absorption for various treated alkoxide solutions.

FIG. 5 is the infrared absorption spectrum diagram of the films obtained. The curve (a) shows the spectrum of the film which has been subjected to light radiation neither at the stage of the reaction solution nor after the film formation, the curve (b) the spectrum of the film in accordance with the present invention which has been subjected to light radiation twice, and the curve (c) the spectrum of the film which has been formed from the reaction solution which has not been irradiated with light and which has been heat treated at 400° C. in air after the film formation. As shown in FIG. 5, the intensities of the spectral lines of (a) and (b) are lower in the vicinity of the wave numbers of 3300 cm$^{-1}$ and 1600 cm$^{-1}$ respectively than that of (c). This is due to the presence of water. In (a), the C—H oscillation due to an organic substance is observed. In other respects, the polymer films of Ta oxides show the same absorption spectrum.

FIGS. 6 to 9 show the dielectric constants ($\epsilon$), withstand voltages (MV/cm), TaOx compositions and C contents in the films, respectively, of the Ta oxide films obtained by various methods. The films are as follows:

An optical CVD film formed at 200° to 300° C.

B. Thermal CVD obtained by film formation at 350° C.

C. A heat-treated sol-gel film obtained by heat treating at 400° C. the film formed from the reaction solution without light radiation.

D. and E. Light-assisted sol-gel films obtained by the process shown in FIG. 2 in accordance with the present invention, the films having been irradiated respectively in nitrogen (film D) and in oxygen (film E) after the film formation.

F. A sol-gel film obtained by 6-hour reaction without light radiation or heat treatment.

Each sol-gel film was formed in 4 cycles of layer formation and had a thickness of 2000 Å.

Figure 6:
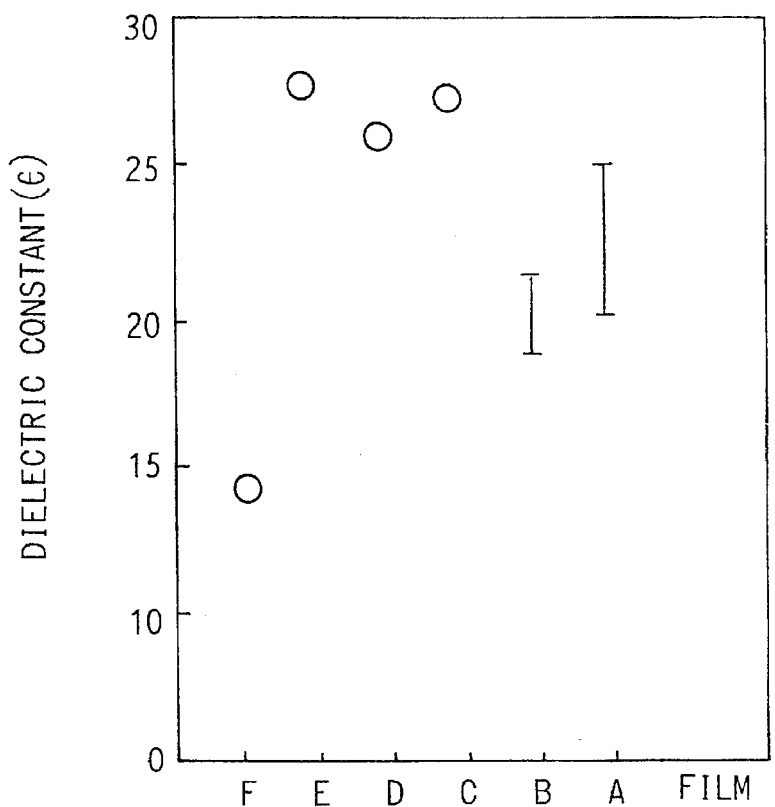
FIGS. 6 to 9 show the dielectric constants, withstand voltages, C contents and TaOx compositions, respectively, of the metal oxide films obtained by various methods.

As shown in FIG. 6, the films of the present invention (D,E) exhibit a dielectric constant ($\epsilon$) of not less than 25, which is as high as that of the heat-treated film (C), but the CVD films (A,B) and the sol-gel film (F) have a lower dielectric constant.

Figure 7:
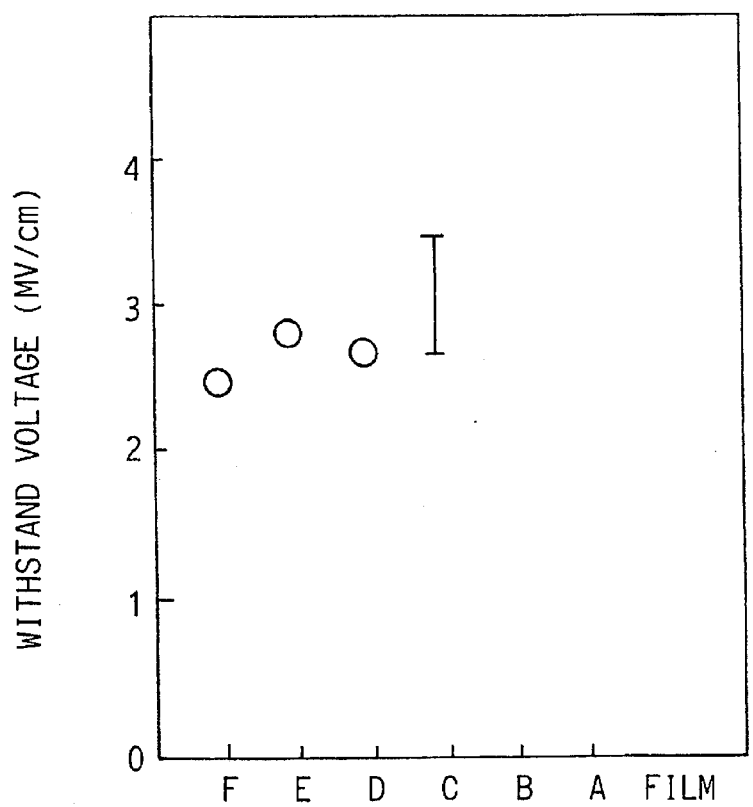

As shown in FIG. 7, the films of the present invention (D,E) provide a withstand voltage of not less than 2.7 MV/cm.

Figure 8:
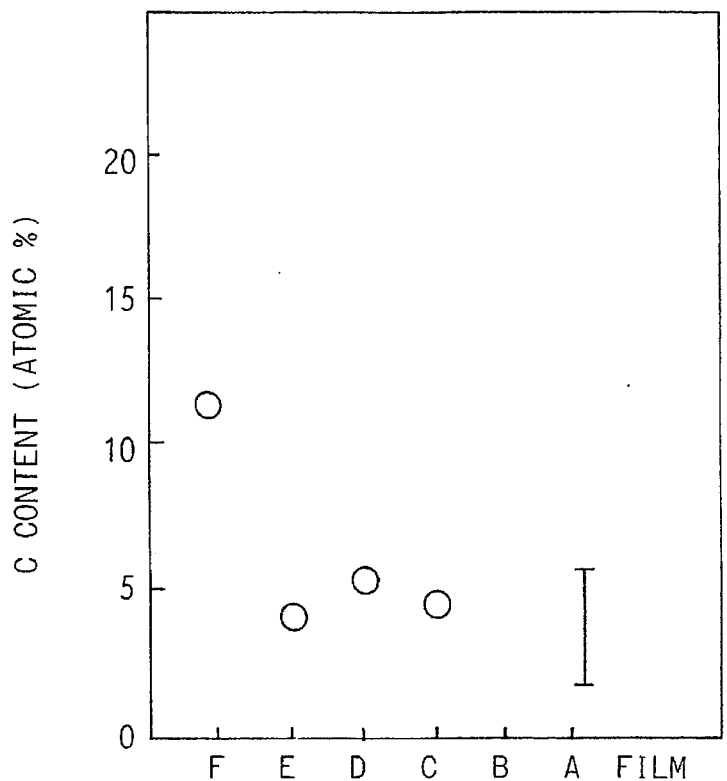

As shown in FIG. 8, the C content in the film of the present invention is as low as 4 atomic %, especially, in the case of the $O_2$ light-assisted film (E), which has a low C content similar to that of the heat-treated film.

Figure 9:
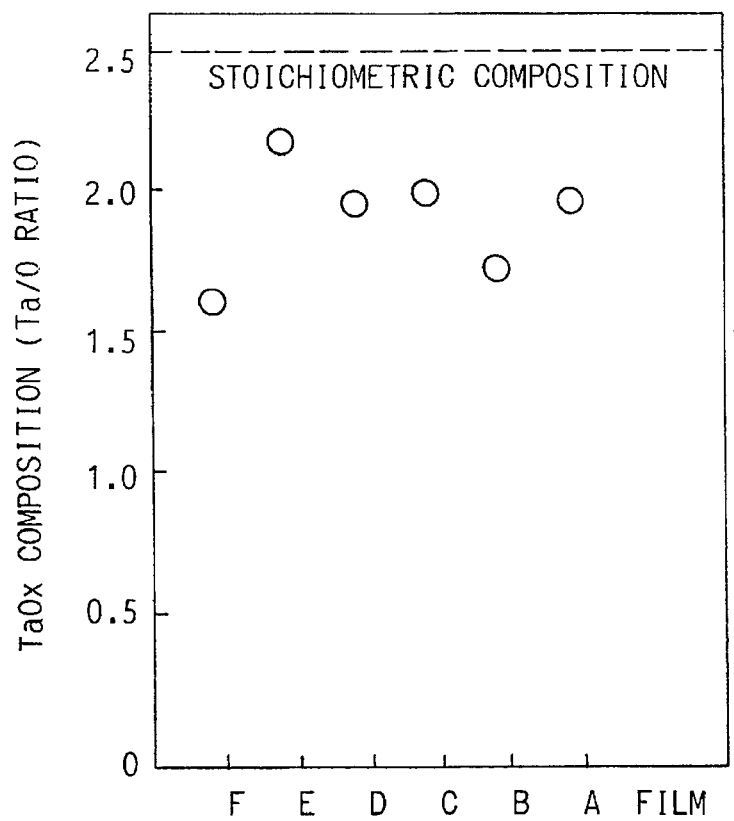

As shown in FIG. 9, the x-value of the TaOx composition of the $O_2$ light-assisted film (E) is 2.2, which is 88% of the stoichiometrical oxygen quantity of 2.5. It is thus possible to obtain a film having a higher stoichiometrical ratio than the heat-treated film (C), which has the TaOx composition of 2.0, namely 80% of the stoichiometrical oxygen quantity.

The resistivity of the $O_2$ light-assisted film of the present invention has as high a value as $10^{11}$ $\Omega$cm.

As is apparent from the above-described results, therefore, the light-irradiated film (E) of the present invention in this Example contained C—H bonding, and the amount of organic substance therein was 4.0 atomic % measured as C content and the TaOx composition ratio (O/Ta) was 2.2.

On the other hand, the film (F) which had not been subjected to light radiation contained C—H bonding, the amount of organic substance therein was 11.0 atomic % measured as C content and TaOx composition ratio (O/Ta) was 1.6. The light-irradiated film of the invention thus exhibits 0.36 and 1.4 times the amount of residual organic substance and the TaOx composition ratio (O/Ta), respectively, of the film which has not been subjected to light radiation. In other words, a film having a small amount of residual organic substance and TaOx composition ratio approximate to the stoichiometrical ratio was obtained. In order to obtain a film having the same amount of residual organic substance and the same TaOx composition ratio as the light-irradiated film, it was necessary to heat treat the film which had not been subjected to light radiation at not lower than 400° C.

Lower values of residual C than shown in FIG. 8 are obtainable with the invention. A film made as described with reference to FIG. 2 and subsequently irradiated with UV radiation of intensity 40 mW/cm$^2$ for three hours showed on analysis a residual C content of 0.01 atomic %.

By the same method, thin films were formed on organic substrates having a heat resistance of not lower than 300° C. such as substrates of a polyester film, a Mylar sheet and an acrylic resin, and a metal substrate having a difference in the thermal expansion coefficient from the film of not less than $5 \times 10^{-6}$ K$^{-1}$ such as a stainless steel substrate (thermal expansion coefficient $17.3 \times 10^{-6}$ K$^{-1}$), and an aluminum substrate (thermal expansion coefficient $23.6 \times 10^{-6}$ K$^{-1}$). These films exhibited similar amounts of residual organic substance and similar TaOx composition ratios to those of the film formed on the SiO$_2$ substrate.

EXAMPLE 2

A transparent conductive film was deposited on a glass substrate (34 mm×34 mm) and was subjected to photoetching to produce the glass plate provided with a transparent conductive film 2 mm wide.

Using the thus-obtained glass substrate, an electroluminescence element (hereinunder referred to as "EL element") shown in FIG. 10(A) and 10(B) was produced.

On the glass substrate 13 provided with the transparent conductive film 14, a tantalum pentoxide film was formed by using the reaction solution of Example 1 which had been subjected to light irradiation for 60 minutes as described. The process shown in Example 1 was repeated four times to form an amorphous polymeric Ta$_2$O$_5$ film to a thickness of 200 nm on the transparent conductive film as a first insulating layer 15 of the EL element. After depositing ZnS containing 0.5 wt % of Mn to a thickness of 500 nm as a light-emitting layer 16, the glass substrate was subjected to vacuum heat treatment for 1 hour at $2.6 \times 10^{-4}$ Pa and 300° C. Further, a second insulating film 17 was formed by sputtering BaTa$_2$O$_6$ to a thickness of 200 nm. After upper electrodes 18 200 nm thick were formed by the resistance heating deposition of aluminum, an electrode terminal was attached, thereby producing the EL element.

In the plan view of the EL element of FIG. 10 (B), the intersections of the transparent conductive film 14 and the upper electrodes 18 correspond to picture elements, which emit light.

In a conventional EL element, since a Y$_2$O$_3$ film having a dielectric constant of about 12 and a withstand voltage of about 3 to 5 MV/cm is used for the first insulating layer and the second insulating layer, a voltage as high as about 200 V is required for driving the EL element. In the element of the present embodiment of the present invention, the Ta$_2$O$_5$ film used for the first insulating layer had a dielectric constant of 28 and a withstand voltage of 2.8 MV/cm, so that it was possible to drive the element at a voltage as low as 170 V. On the other hand, in a similar EL element using the Ta$_2$O$_5$ film which had not been subjected to light radiation for the first insulating layer, the dielectric constant was 14 and the withstand voltage was as low as 2.3 MV/cm even after the heat treatment at 300° C. after the deposition of the light emitting layer, so that a driving voltage of 210 V was necessary.

As the light emitting layer, ZnS with $Sm^{3+}$ (red), $Tb^{3+}$ (green), $Tm^{3+}$ (blue) or the like added may be used, as well as Eu-containing CaS (red), Ce-containing CaS (green) and Ce-containing SrS (blue green)

A polymeric film of $SiO_2$ or $Y_2O_3$ is usable as the insulating layer 15 instead of the $Ta_2O_5$, and amorphous films having an oxygen content as high as not less than 85% of the stoichiometrical composition with respect to $SiO_2$ and $Y_2O_3$ are similarly obtained by the sol-gel method of the present invention.

In order to form the transparent conductive film 14, light having a wavelength of 230 to 240 nm was radiated onto a solution of a mixture of tin alkoxide ($Sn(OC_2H_5)_4$) and indium alkoxide ($In(OCH)_3)_3$) for 60 minutes to prepare the prepolymer solution of tin oxide and indium oxide. The glass substrate 13 was then dipped into the solution to form a film, and ultraviolet radiation having a wavelength of 184 nm was directed onto the film. After this process was repeated to form the transparent conductive film 14 having a predetermined film thickness, the transparent conductive film was completed in the same way as in the case of the first insulating layer described above. The light emitting layer 16 and the second insulating layer 17 is formed in the same way as described above.

The EL element has a multiplicity of picture elements formed on the substrate, and is driven by a high-frequency power source. The EL element is further provided with an $SiO_2$ protective film on the entire surface thereof. The protective film may also be composed of a polymeric amorphous film formed in accordance with the present invention as described above.

As described above, in the EL element produced in this embodiment, the transparent conductive film 14 and the insulating films 15,17, though not the light emitting layer and the upper electrode, may be composed of a polymeric amorphous films by the sol-gel method of the invention which dispenses with heat treatment. Therefore, it is advantageously possible to produce the EL element with little thermal influence due to differences in the thermal expansion coefficient.

EXAMPLE 3

A $Ta_2O_5$ film 20 was formed on a substrate 19 of Si (P-type, face index: (100), resistivity: 1.2 to 1.8 Ω.cm) by the method described in Example 1, as shown in FIG. 11. The solution subjected to light radiation for 60 minutes as described in Example 1 was used and the process was repeated four times to form the $Ta_2O_5$ film on the Si substrate to a thickness of 200 nm. Then an Al electrode 21 was deposited on the insulating film 20 to a thickness of 100 nm in vacuum, and an Al electrode 21 was similarly deposited on the rear side of the substrate, thereby forming a thin film capacitor.

The dielectric constant of the insulating layer 20 was 28, which is 5 times as large as that of an $SiO_2$ layer, and the withstand voltage was 2.8 MV/cm, which is also larger than that of a conventional $Ta_2O_5$ layer. By using the insulating film 20 according to the present invention, a thin film capacitor having a large static capacity per unit area and a good withstand voltage characteristic can be obtained.

EXAMPLE 4

The inner surface of a SUS 304 stainless steel beaker (inner diameter: 50 mm, depth: 60 mm) was coated with a $Ta_2O_5$ film of about 200 nm thick by repeating the process described in Example 3 four times. 20 ml of 3 N hydrochloric acid was charged into the stainless steel beaker and the opening was sealed with a film. Then the beaker was allowed to stand for one month, whereafter the hydrochloric acid was discharged and the inner surface of the beaker was observed. No corrosion was observed on the surface of the stainless steel. That is to say, the corrosion resistance was improved by the coating of the $Ta_2O_5$ film by the method according to the present invention.

When a similar experiment was carried out to form a $Ta_2O_5$ film using the solution which had not been subjected to light radiation, the durability of the film on the stainless steel was poor. After 7 days, the film was separated from the surface and corrosion was also observed. When the beaker was heat treated at 200° C. in order to enhance the adhesion of the film, the film separated from the surface, which is considered to have been caused by the difference in the thermal expansion coefficient between the stainless steel and the thin film.

The $Ta_2O_5$ film in accordance with the present invention is effective as a protective film against oxidization in air and corrosion not only for SUS 304 stainless steel but also for all other steels, e.g. a carbon steel, and for other metals e.g. Al and Cu and their alloys against oxidization and corrosion. Although a $Ta_2O_5$ film is cited as an example in this embodiment, the other film materials such as described above can be selected as an oxide film in accordance with the kind of the material being coated.

EXAMPLE 5

An ethanol solution of 0.5 mol/l of silicon tetraethoxide was prepared. To 20 ml of the solution, a mixed solution of 80 ml of ethanol solution of 0.5 mol of water and 10 ml of ethanol solution of 0.1 mol/l of hydrochloric acid was added dropwise at a rate of 3 ml/min to obtain a transparent uniform mixed solution. The mixed solution was irradiated with light having a wavelength of 210 nm, which corresponds to the silicon-ethoxy group absorption frequency, for 60 minutes using the film-forming apparatus shown in FIG. 1. The intensity was 10 $mW/cm^2$. Thereafter, a semiconductor device composed of a silicon substrate 24 and a thin film integrated circuit comprising $SiO_2$ and electrode layers 25,26 formed thereon as shown in FIG. 12 was dipped into the solution by using the dipping device attached to the film-forming apparatus to form a thin film 27 of polymeric $SiO_2$ on the integrated circuit, and was irradiated with light having a wavelength of 184 nm for about 10 minutes at 3 $mW/cm^2$ in order to generate ozone in air. The polymeric $SiO_2$ film 27 is a protective film of $SiO_2$ produced by the method of the present invention, and is for protecting the thin film integrated circuit from external disturbance. This film 27 has a very pure composition approximate to the stoichiometrical ratio of Si and O and has a higher polymerization degree than a conventional $SiO_2$ film, so that its protective property is excellent. In addition, the film is not subjected to heat treatment after formation unlike in the prior art, so that it is free from stress and the diffusion of impurities such as $Na^+$ which may be generated during the heat treatment and will exert deleterious influence on a semiconductor device. It is therefore possible to achieve the reduction in the soft error of the device to not more than 75 fits. The $SiO_2$ film 25 is formed by thermal oxidation, and the Al electrodes 26 were formed by deposition, sputtering or the like.

EXAMPLE 6

An isopropyl alcohol solution of 1 mol/l of tripropoxyantimony was prepared. To 30 ml of the solution, a mixed solution of 15 ml of isopropyl alcohol solution of 1 mol/l of water and 5 ml of isopropyl alcohol solution of 0.1 mol/l of hydrochloric acid was added dropwise at a rate of 3 ml/min to obtain a transparent uniform mixed solution. The mixed solution was irradiated with light having a wavelength of 250 nm, which corresponds to the antimony-isopropyl group absorption wavelength for 30 minutes at 10 mW/cm$^2$ using the film-forming apparatus shown in FIG. 1. Thereafter, a polymethyl methacrylate resin (PMMA) substrate 28 (diameter: 130 cm, thickness 1 mm) shown in FIG. 13 was dipped into the solution using the dipping device attached to the film-forming apparatus to form a thin film 29 on the PMMA substrate, and this film was irradiated with light having a wavelength of 184 nm for about 10 minutes at 3 mW/cm$^2$ in order to generate ozone in air. In this way, a recording medium layer 100 nm thick was formed on the PMMA substrate. A similar thin film 29 was formed on another PMMA substrate 28. The two substrates were bonded to each other through spacers 30 to produce an optical disk having the structure shown in FIG. 13. The optical disk, which is provided with polymeric antimony oxide thin films having a highly stoichiometrical composition and a good adhesion with the substrate without being subjected to heat treatment, has a long-time reliability.

To use a metal oxide as a memory material, i.e. a recording material, it is possible by a similar method to obtain an oxide mainly containing a Te oxide and having 1 to 10 wt % of at least one element selected from Ga, Ge and As and 10 to 20 wt % of at least one element selected from In, Sn and Sb.

To provide a protective film on the recording medium, it is possible to form a polymeric film of $SiO_2$ in the same way as in Example 5. It is also possible to form a protective film on the entire surface of a disk.

EXAMPLE 7

A 20 ml ethanol solution of 0.5 mol/l silicon ethoxide and 20 ml ethanol solution of 0.5 mol/l titanium ethoxide were mixed. To this mixture a mixed solution composed of 20 ml ethanol solution of 0.5 mol/l water and 1 ml ethanol solution of 0.1 mol/l hydrochloric acid was slowly added at a rate of 0.2 ml/minute. Into the thus produced uniform mixture solution a polyethylene substrate (50 mm×50 mm×2 mm (thickness)) was located at the position 5 mm below the liquid surface. Next a light beam having a wavelength of 210 nm corresponding to the absorption wavelength of the silicon-ethoxy bond was irradiated from above the liquid surface for 10 minutes at 15 mW/cm$^2$. Thereafter the substrate was taken out and irradiated for 10 minutes with a light beam having a wavelength of 184 nm which is suitable for ozone oxidation at intensity of 3 mW/cm$^2$. This treated substrate was again located at the position 5 mm below the liquid surface and then was irradiated with a light beam having a wavelength of 260 nm corresponding to the absorption wavelength of the titanium-ethoxy bond for 10 minutes at 15 mW/cm$^2$. Then the substrate was taken out and was irradiated for 10 minutes with a light beam having a wavelength of 184 nm for ozone oxidation at 3 mW/cm$^2$. These steps of irradiating alternately the light beams having wavelengths of 210 nm, 184 nm, 260 nm, and 184 nm were repeated five times. FIG. 14 shows the structure of the multi-layered film thus produced. On the polyethylene substrate 31 are layers 32 containing a large amount of $SiO_2$ (also containing $TiO_2$) and layers 33 containing a large amount of $TiO_2$ (also containing $SiO_2$). The multi-layered film thus produced on the polyethylene substrate showed a good performance as a reflection prevention film with light weight and with high strength. Further identification of the chemical species $SiO_2$ and $TiO_2$ was carried out with ESCA and as a result Si(IV) and Ti(IV) were observed.

EXAMPLE 8

20 ml ethanol solution of 0.5 mol/l indium ethoxide and 20 ml ethanol solution of 0.5 mol/l tin ethoxide were mixed. To this solution, a mixed solution composed of 20 ml ethanol solution of 0.15 mol/l water and 1 ml ethanol solution of 0.1 mol/l hydrochloric acid was slowly added at the rate of 0.2 ml/minute. Into the thus produced uniform mixed solution a polyethylene substrate (50 mm×50 mm×2 mm (thickness)) was located at the position 5 mm below the liquid surface. Next a light beam having a wavelength of 270 nm corresponding to the absorption wavelength of the indium-ethoxy bond was irradiated from above the liquid surface for 10 minutes at 15 mW/cm$^2$ Thereafter the substrate was taken out and irradiated for 10 minutes with a light beam having a wavelength of 184 nm for ozone oxidation at 3 mW/cm$^2$. Again this substrate was located at the position 5 mm below the liquid surface and then was irradiated with a light beam having a wavelength of 230 nm corresponding to the absorption wavelength of the tin-ethoxy bond for 10 minutes at 15 mW/cm$^2$. Then the substrate was taken out and was irradiated for 10 minutes with a light beam having a wavelength of 184 nm for ozone oxidation at 3 mW/cm$^2$. These steps for radiation with the various light beams in solution and in air alternately were repeated five times. FIG. 15 shows the structure of multi-layered film thus produced. The polyethylene substrate 34 has layers 35 containing a large amount of $In_2O_3$ (also containing $SnO_2$), and layers 36 containing a large amount of $SnO_2$ (also containing $In_2O_3$). The multi-layered film thus produced on the polyethylene substrate showed a good performance as a reflection preventing film of light weight and of high strength.

FIG. 16 is a constructional diagram showing an example of apparatus for practicing the present invention. The apparatus has a light source 61 provided with a system for controlling requirements such as irradiation position, scanning speed, beam diameter and wavelength in order to form a predetermined shaped body, a substrate 62 for forming the shaped body thereon, a substrate supporting stand 63 provided with an upward and downward shifting mechanism which can hold the substrate 62 and immerse it into and pull it out of sample solutions 64 and 65, and to enable the formation of the predetermined shaped body by cooperating with the light source 61. Stirring bodies 66 and stirrers 67 are provided for maintaining the sample solutions homogeneous. These parts are arranged in a box 68. The box is provided with an opening 69 and atmosphere adjusting means which enables it to be maintained with an inert atmosphere.

Light beams generated from the light source 61 are irradiated onto the coated substrates 62 which are immersed in the respective sample solutions. A system is employed in which the irradiation position is automatically shifted under a predetermined condition.

EXAMPLE 9

20 ml ethanol solution of 0.5 mol/l indium ethoxide and 20 ml ethanol solution of 0.5 mol/l tin ethoxide were mixed. To this mixed solution, a mixed solution composed of 20 ml ethanol solution of 0.5 mol/l water and 1 ml ethanol solution of 0.1 mol/l hydrochloric acid was slowly added at the rate of 0.2 ml minute. In this manner a homogeneous mixture solution A was prepared. Next epoxy acrylate resin solution B (specific gravity of 1.14, viscosity of 200 cps (20° C.)) was prepared.

Using the above A and B as the sample solutions a transparent member with a built-in conductive layer was formed through the predetermined shaped body forming apparatus shown in FIG. 16. The product is shown in FIGS. 17A and B.

The above solution A was supplied as solution 64 of FIG. 16 and B as solution 65. An acrylic resin plate 70 (FIGS. 17A and B) was used for the substrate. First of all the substrate 70 was immersed in solution 64, then pulled out and irradiated with a HeCd laser beam (output of 30 mW, beam width 10 μm, exposure time $1\times10^{-4}$ s) at the scanning velocity of 100 mm/s. Following this the substrate was scanned with a light beam having a wavelength of 184 mm at the scanning velocity of 10 mm/s. By repeating these operations five times, an indium-tin oxide (ITO) layer 71 was formed on the acrylic resin plate 70. The ITO layer 71 formed on the acrylic resin plate had a thickness of 0.5 μm and a width of 30 μm and a pattern as illustrated in FIG. 17(A).

After the ITO layer 71 was formed, the substrate was immersed in solution 65 and its whole surface was irradiated with the HeCd laser beam and by repeating this twice an epoxyacrylate resin coating layer 72 of 0.1 mm thickness was formed. Prevention of clouding on the substrate was achieved by conducting a current between two terminal portions of the ITO.

EXAMPLE 10

To a solution of polyvinyl butyral dissolved in ethanol containing 1% of water, ethanol solution of tantalum ethoxide $(Ta(OC_2H_5)_5)$ was added and sufficiently stirred to obtain a mixed solution. After the viscosity of this solution was adjusted to about 5000 cps during a vacuum defoaming operation, the solution was formed into a sheet shape on a polyester sheet by the well known doctor blade method. At this time, the surface of the sheet was irradiated at the outlet of the blade with a Kr—F laser beam of wavelength 249 nm at the scanning velocity of 100 mm/s, and then irradiated with a light beam having a wavelength of 184 nm from an ultra violet lamp at the scanning velocity of 10 mm/s. After thus effecting the chemical reactions, a sheet having a thickness of 30 μm, a length of 1000 mm and a width of 10 mm was obtained after drying thereof. The dielectric constant of this sheet was 6.1 which is larger than that of polyvinyl butyral itself, which is 3.6.

On one face of the formed sheet aluminum was deposited. Two sheets produced in the same manner were laminated and rolled, then heated at about 80° C. and pressed at 20 kg/cm² so as to increase adhesion between the sheets. Thereafter at both ends thereof aluminum external electrodes were formed through metallization, and lead wires were soldered to the respective electrodes to obtain a condenser.

The condenser thus formed has a high condenser capacity because the inorganic material was homogeneously complexed with the organic material in the sheet. The dielectric constant of the dielectric body itself was increased in comparison with the conventional condenser employing a film made only from an organic material.

EXAMPLE 11

By using the solution A and the resin B as prepared in Example 9, a touch panel illustrated in FIG. 18 is produced by the following method.

First, the mixture solution A was coated on a polyester sheet 73 through the doctor blade method. At this time the coated layer on the sheet was irradiated at the outlet of the blade with Kr—F laser beam (wavelength 249 nm) at a scanning velocity of 100 mm/s, and then irradiated with a light beam having a wavelength of 184 nm from an ultra violet lamp at a scanning velocity of 10 mm/s. By repeating this operation four times, a transparent conductive film 74 (ITO film) having a thickness of 0.5 μm was formed on the polyester sheet. Following this, the resin B was coated on the ITO film and the coated face was irradiated with a He—Cd laser beam having an irradiation diameter of 0.3 mm at an interval of 5 mm, to provide spaced portions 75 of epoxyacrylate resin, which serve as spacers for the touch panel. Thus a structural member having a cross sectional configuration as shown in FIG. 18 was formed.

In the same manner, a similar member having an ITO film formed on a polyester sheet was produced. After formation of electrodes, the two were combined to obtain a touch panel. The touch panel formed by this method satisfied requirements in respect of its responsiveness, transparency and other properties.

EXAMPLE 12

20 ml ethanol solution of 0.5 mol/l silicon ethoxide, 20 ml ethanol solution of 0.5 mol/l water and 1 ml ethanol solution of 0.1 mol/l hydrochloric acid were mixed. Into the resulting homogeneous solution an aluminum conductor wire was immersed. When the wire was lifted out from the solution, it was irradiated with an Ar—F laser beam (wavelength 193 nm) at the boundary of the solution. The lifting velocity of the wire was 60 mm/s. Thereafter the wire was irradiated with an ultraviolet light beam having a wavelength of 184 nm, and by repeating these operations five times an insulation film of $SiO_2$ was formed on the surface of the conductive wire. When this insulation film was tested at 600° C., its insulating property was maintained, and since it did not emit hydrocarbon and carbon dioxide it could be used in a vacuum environment.

Thus, by the method of the present embodiment a coating layer was confirmed to be successfully formed at a low temperature on the wiring material.

EXAMPLE 13

20 ml ethanol solution of 0.5 mol/l silicon ethoxide, 20 ml ethanol solution of 0.5 mol/l water and 1 ml ethanol solution of 0.1 mol/l hydrochloric acid were mixed to prepare a solution (I). Ethanol solution of 0.5 mol/l titanium ethoxide, ethanol solution of 0.5 mol/l water and ethanol solution of 0.1 mol/l hydrochloric acid were added to prepare a solution (II).

First a polyester substrate was located at the position 5 mm below the liquid surface of the solution (I), and was irradiated from above the liquid surface with a light beam having a wavelength of 210 nm corresponding to the absorption wavelength of the silicon-ethoxy bond for 10 minutes. Thereafter the substrate was taken out from the solution and was irradiated for 10 minutes with a light beam having a wavelength of 184 nm for ozone oxidation. The substrate was then located at the position 5 mm below the liquid surface of the solution (II), and was irradiated with a light beam having a wavelength of 260 nm corresponding to the absorption wavelength of the titanium-ethoxy bond for 10 minutes. Next the substrate was taken out from the solution and was irradiated for 10 minutes with a light beam having a wavelength of 184 nm for ozone oxidation. The four irradiation steps were repeated five times. Thereby a multi-layer film of alternating $SiO_2$ layer / $TiO_2$ layer was formed on the polyester substrate. This multi-layered film showed a good property as a reflection preventing film.

EXAMPLE 14

An environmental protective film was produced on a plastics optical fiber. FIG. 19 is a cross-sectional view of the plastics optical fiber with the protective film thus produced and shows the protective film 81, an organic resin portion 82, a clad portion 83 and a core portion 84. A method for producing the protective film is explained below.

An ethanol solution of 0.5 mol/l silicon ethoxide was prepared. Into 10 ml of this solution, a mixture of 80 ml ethanol solution of 0.5 mol/l water and 10 ml ethanol solution of 0.1 mol/l hydrochloric acid was dropped at the rate of 3 ml/minute to obtain a transparent homogeneous solution. This solution was irradiated with a light beam having a wavelength of 210 nm for 60 minutes at 10 $mW/cm^2$ using the film-forming device shown in FIG. 16. A plastics optical fiber 82,83,84 (diameter: 2 mm) was immersed in this solution and a $SiO_2$ protective film 81 was formed on the surface of the fiber. Next, this fiber was irradiated in air for 10 minutes with a light beam having a wavelength of 184 nm and intensity 3 $mW/cm^2$ for generating ozone. An environmental resistance test of the plastics optical fiber thus obtained was performed in an engine oil at a temperature of 100° C. FIG. 20 shows the results of the test. The ordinate shows an optical amount holding ratio and the abscissa shows the lapsed time (hours). The light retention ratio of an optical fiber without such a protective film reduced to about 40% after 1000 hours due to diffusion of the oil into the fiber. The optical fiber with the protective film produced according to the present example showed an extremely good oil resistance, in that the light retention ratio is maintained at more than 80% even after 1000 hours. Therefore the product is for example suitable as a plastics optical fiber for automobile engine control. Further since the present film forming method is a low temperature process, formation of an inorganic film on a plastic fiber having a low thermal resistance is made possible.

EXAMPLE 15

According to a conventional production process for a plastic molded type semiconductor element, after attaching a chip and a pellet to a lead frame, an Au wire is wirebonded thereto. On this element an inorganic film was undercoated by using the following method as shown in FIG. 21.

Ethanol solution of 0.5 mol/l silicon tetraethoxide was prepared. To 20 ml of this solution 80 ml ethanol solution of 0.5 mol/l glacial acetic acid i.e. organic acid, was slowly added. To this mixed solution, a light beam having a wavelength of 210 nm corresponding to the absorption energy of the silicon-ethoxy radical bond was irradiated for 30 minutes at 15 $mW/cm^2$. By immersing the above-described semiconductor element in this solution an inorganic protective film 95 was formed. Next, this element was irradiated in the air with a light beam having a wavelength of 184 nm for 10 minutes at 3 $mW/cm^2$ The element was again immersed in the solution to form a film and then was again irradiated in the air with a light beam having a wavelength of 184 nm for 10 minutes. By repeating this process ten times the undercoat was formed. The element thus produced was resin-sealed with an epoxy resin to complete the semiconductor element. FIG. 21 shows this structure, which has a lead frame 91, an Au wire 92, an Au—Si alloy 93, a chip 94, the inorganic protective film 95 and the epoxy resin 96.

The present method includes no heat treatment process, and no water is contained in the solution which was used for the formation of the inorganic protective film, so that a semiconductor element having an excellent performance was obtained. Since no stress is generated, which otherwise may be generated in a heat treatment process, and wettability between the Au wire and the inorganic protective film is good, a protective film with a high adhesiveness was produced. Moreover since no water is present in the protective film, reduction of soft errors in the element was achieved.

EXAMPLE 16

A $Ta_2O_5$ thin film condenser for a high frequency use was produced according to the method of the present invention.

Ethanol solution of 0.5 mol/l tantalum ethoxide was prepared. To 20 ml of this solution 90 ml ethanol solution of 0.5 mol/l glacial acetic acid was added. To this mixed solution a light beam having a wavelength of 254 nm was irradiated for 60 minutes at 10 $mW/cm^2$. Into this solution a Fe-42%Ni plate 101, of which the back face was masked, was immersed to form a film as shown in FIG. 22. The face with the film was irradiated in air with a light beam having a wavelength of 184 nm for 10 minutes at 3 mW/cm By repeating this process, a $Ta_2O_5$ film 102 of 1 µm thickness was produced. The thin film condenser was completed by vacuum evaporating Al metal 103 onto the Fe-42%Ni plate having the $Ta_2O_5$ film. In this thin film condenser, substantially no static capacitance change was observed even at 1 GHz. Therefore in a high speed electronic device or a high density circuit, this thin film condenser can provide a counter measure to noise which is a major cause of erroneous operation.

EXAMPLE 17

A protective film was produced on a plastics lens. FIG. 23 is a cross sectional view of the plastics lens 111 with the protective film 112 produced according to the present example. The method for producing the protective film on the lens is as follows.

Ethanol solution of 0.5 mol/l silicon ethoxide was prepared. To 20 ml of this solution a mixed solution of 80 ml ethanol solution of 0.5 mol/l water and 10 ml ethanol solution of 0.1 mol/l hydrochloric acid was dropped at a rate of 3 ml/minute to obtain a transparent homogeneous solution. To this solution a light beam having a wavelength of 210 nm was irradiated for 60 minutes at 10 $mW/cm^2$ using the film forming device shown in FIG. 16. Then a plastic lens (diameter of 100 mm, maximum convex portion of 5 mm), of which the concave face is protected by a tape so as not to contact the solution, was immersed into this solution and the $SiO_2$ protective film 112 was formed on the convex face of the plastic lens 111. Thereafter, this lens was irradiated in air with a light beam having a wavelength of 184 nm for ozone generation for 10 minutes at 3 $mW/cm^2$. Since the protective film thus produced on the plastic lens is fine and hard, no scratch is caused on the lens in normal use, enabling the useful life to be greatly prolonged. With the present method a uniform film can, if desired, be formed on the concave portion as well.

EXAMPLE 18

A $Ta_2O_5$ thin film condenser was produced on a printed circuit substrate according to the method of the present invention.

An ethanol solution of 0.5 mol/l tantalum ethoxide was prepared. To 20 ml of this solution 80 ml ethanol solution of 0.5 mol/l glacial acetic acid was added. To this mixture a light beam having a wavelength of 254 nm was irradiated for 60 minutes. Then a printed circuit substrate, of which the entire back face and a portion of front face where a ground electrode of silicon chip is earthed were masked, was immersed into this solution, and a $Ta_2O_5$ film was formed on the surface of the printed wire substrate. The face having the film was irradiated in air with a light beam having a wavelength of 184 nm for 10 minutes. Again this substrate was immersed in the solution to form a film, and thereafter irradiated in air with a light beam having a wavelength of 184 nm. By repeating this process ten times a $Ta_2O_5$ film of 0.5 μm thickness was produced. Next, after removing the mask material, Al was vacuum evaporated onto the upper side of $Ta_2O_5$ film and the portion from which the mask was removed to form electrodes. On top thereof a silicon chip was mounted. FIG. 24 is a cross-sectional view of the silicon chip of the printed circuit substrate thus produced. FIG. 24 shows a printed circuit substrate 121, electrodes 122, the $Ta_2O_5$ film 123 as a dielectric material layer, and the silicon chip 124. The $Ta_2O_5$ functions as a thin film condenser and no static capacitance change was observed even at 1 GHz. Thereby, the semiconductor element produced according to the above method achieved a reduction of noise which is a major cause of erroneous operations when a high speed device and circuit are mounted at high density.

EXAMPLE 19

A substrate for a semiconductor mounting provided with an insulation layer of a metal oxide film on a copper plate was produced by the method of the present invention.

An ethanol solution of 0.5 mol/l silicon ethoxide was prepared. To 20 ml of this solution, 90 ml ethanol solution of 0.5 mol/l glacial acetic acid, i.e. an organic acid, was slowly added. To this mixed solution, a light beam having a wavelength of 210 nm was irradiated for 30 minutes at 12 mW/cm². Then a copper plate of a predetermined size was immersed in the solution to form a $SiO_2$ film. Then, this substrate was irradiated in the air with a light beam having a wavelength of 184 nm for 10 minutes at 3 mW/cm². By repeating this process, i.e. immersion film forming and light beam irradiation in air, twenty times a $SiO_2$ film of about 10 μm thickness was produced on the copper plate. This substrate is suitable for semiconductor mounting, because the insulator layer of $SiO_2$ formed on the copper has a good thermal conductivity. Therefore heat generated during the operation of the semiconductor element is efficiently removed. FIG. 25 shows the semiconductor element produced by using this substrate. FIG. 25 shows silicon chips 131, bonding wires 132, leads 133, $SiO_2$ film 134, copper substrate 135, sealing glass 136, metal wiring layer 137, cap 138, cooling fins 139 and bonding layer 140.

What is claimed is:

1. A display unit comprising the display units substrate and a film thereon having a thickness of 1 to 1000 nm and consisting essentially of a polymeric metal oxide containing C—H bonds, said metal oxide having a total carbon content of 0.01 to 4 atomic %.

2. A liquid crystal display device comprising the liquid crystal display device substrate and a film thereon having a thickness of 1 to 1000 nm and consisting essentially of a polymeric metal oxide containing C—H bonds, said metal oxide having a total carbon content of 0.01 to 4 atomic %.

* * * * *